United States Patent
Sarfarazi

(10) Patent No.: US 7,662,179 B2
(45) Date of Patent: *Feb. 16, 2010

(54) HAPTICS FOR ACCOMMODATIVE INTRAOCULAR LENS SYSTEM

(76) Inventor: Faezeh M. Sarfarazi, 7461 Mermaid La., Carlsbad, CA (US) 92009

( * ) Notice: Subject to any disclaimer, the term of this patent is extended or adjusted under 35 U.S.C. 154(b) by 0 days.

This patent is subject to a terminal disclaimer.

(21) Appl. No.: 10/307,679

(22) Filed: Dec. 2, 2002

(65) Prior Publication Data

US 2003/0130732 A1 Jul. 10, 2003

Related U.S. Application Data

(63) Continuation-in-part of application No. 09/288,560, filed on Apr. 9, 1999, now Pat. No. 6,488,708.

(51) Int. Cl.
*A61F 2/16* (2006.01)
(52) U.S. Cl. ..................... 623/6.34; 623/6.39
(58) Field of Classification Search ............... 623/6.13, 623/6.34, 6.37
See application file for complete search history.

(56) References Cited

U.S. PATENT DOCUMENTS

| | | | |
|---|---|---|---|
| 4,253,199 A | 3/1981 | Banko | |
| 4,254,509 A | 3/1981 | Tennant | |
| 4,271,841 A | 6/1981 | Friedman | |
| 4,298,996 A | 11/1981 | Barnet | |
| 4,373,218 A | 2/1983 | Schachar | |
| 4,409,691 A | 10/1983 | Levy | |
| 4,426,741 A | 1/1984 | Bittner | |
| 4,463,458 A | 8/1984 | Seidner | |
| 4,517,138 A | 5/1985 | Rawlings et al. | |
| 4,517,139 A | 5/1985 | Rawlings et al. | |
| 4,556,998 A | 12/1985 | Siepser | |
| 4,575,373 A | 3/1986 | Johnson | |
| 4,603,697 A | 8/1986 | Kamerling | |
| 4,666,445 A | 5/1987 | Tillay | |
| 4,680,149 A | 7/1987 | Rawlings et al. | |
| 4,710,193 A | 12/1987 | Volk | |
| 4,720,286 A | 1/1988 | Bailey et al. | |
| 4,790,847 A | 12/1988 | Woods | |
| 4,816,031 A | 3/1989 | Pfoff | |

(Continued)

FOREIGN PATENT DOCUMENTS

DE 195 01 444 A1 7/1996

(Continued)

OTHER PUBLICATIONS

McLeod, et al., A Dual Optic Accommodating Foldable Intraocular Lens, Br. J. Opthalmal, 2003, 87:1083-1085.

(Continued)

*Primary Examiner*—David H. Willse
(74) *Attorney, Agent, or Firm*—DLA Piper LLP (US)

(57) ABSTRACT

An open chamber, accommodative, intraocular lens system operable to be positioned within the interior of an evacuated capsular bag of a human eye. The present invention provides new haptic cross-sections, novel complex lens structures by introduction of the concept of a lens ledge, fixation of haptics to lenses at a lens ledge, structural solutions to provide customized fitted correction, and accordion structural solutions to ease the insertion of complex lenses into the capsular bag of the eye.

18 Claims, 17 Drawing Sheets

U.S. PATENT DOCUMENTS

| | | | |
|---|---|---|---|
| 4,842,601 A | 6/1989 | Smith | |
| 4,888,012 A | 12/1989 | Horn et al. | |
| 4,892,543 A | 1/1990 | Turley | |
| 4,902,293 A | 2/1990 | Feaster | |
| 4,946,469 A | 8/1990 | Sarfarazi | |
| 4,963,148 A | 10/1990 | Sulc et al. | |
| 4,976,732 A | 12/1990 | Vorosmarthy | |
| 4,989,605 A | 2/1991 | Rossen | |
| 4,994,080 A | 2/1991 | Shepard | |
| 4,994,082 A | 2/1991 | Richards et al. | |
| 5,047,051 A | 9/1991 | Cumming | |
| 5,076,683 A | 12/1991 | Glick | |
| 5,108,429 A | 4/1992 | Wiley | |
| 5,109,846 A | 5/1992 | Thomas | |
| 5,152,789 A | 10/1992 | Willis | |
| 5,173,723 A | 12/1992 | Volk | |
| 5,201,762 A * | 4/1993 | Hauber | 623/6.34 |
| 5,203,788 A | 4/1993 | Wiley | |
| 5,275,623 A | 1/1994 | Sarfarazi | |
| 5,275,624 A | 1/1994 | Hara et al. | |
| 5,300,262 A | 4/1994 | Glick | |
| 5,326,347 A | 7/1994 | Cumming | |
| 5,360,438 A | 11/1994 | Fisher | |
| 5,376,115 A | 12/1994 | Jansen | |
| 5,391,202 A | 2/1995 | Lipshitz et al. | |
| RE34,998 E | 7/1995 | Langerman | |
| 5,433,745 A | 7/1995 | Graham et al. | 623/5.16 |
| 5,476,514 A | 12/1995 | Cumming | |
| 5,489,299 A | 2/1996 | Schachar | |
| 5,489,302 A | 2/1996 | Skottun | |
| 5,496,355 A | 3/1996 | Lipsky | 607/53 |
| 5,496,366 A | 3/1996 | Cumming | |
| 5,593,436 A | 1/1997 | Langerman | |
| 5,607,472 A | 3/1997 | Thompson | |
| 5,620,720 A | 4/1997 | Glick et al. | 425/408 |
| 5,628,795 A | 5/1997 | Langerman | |
| 5,674,282 A | 10/1997 | Cumming | |
| 5,728,155 A | 3/1998 | Anello et al. | |
| 5,769,890 A | 6/1998 | McDonald | |
| 5,782,894 A | 7/1998 | Israel | 607/53 |
| 5,843,188 A | 12/1998 | McDonald | |
| 6,013,101 A | 1/2000 | Israel | |
| 6,051,024 A | 4/2000 | Cumming | |
| 6,096,078 A | 8/2000 | McDonald | |
| 6,117,171 A | 9/2000 | Skottun | 623/6.37 |
| 6,136,026 A | 10/2000 | Israel | |
| 6,176,878 B1 | 1/2001 | Gwon et al. | 623/6.37 |
| 6,193,750 B1 | 2/2001 | Cumming | 623/6.43 |
| 6,197,059 B1 | 3/2001 | Cumming | 623/6.39 |
| 6,200,342 B1 | 3/2001 | Tassignon | 623/6.37 |
| 6,217,612 B1 | 4/2001 | Woods | 623/6.37 |
| 6,231,603 B1 | 5/2001 | Lang et al. | 623/6.37 |
| 6,299,641 B1 | 10/2001 | Woods | 623/6.37 |
| 6,322,589 B1 | 11/2001 | Cumming | 623/6.44 |
| 6,342,073 B1 | 1/2002 | Cumming et al. | 623/6.46 |
| 6,387,126 B1 | 5/2002 | Cumming | 623/6.37 |
| 6,391,056 B2 | 5/2002 | Cumming | 623/6.43 |
| 6,406,494 B1 | 6/2002 | Laguette et al. | 623/6.37 |
| 6,413,276 B1 | 7/2002 | Werblin | 623/6.32 |
| 6,423,094 B1 | 7/2002 | Sarfarazi | 623/6.34 |
| 6,428,573 B2 | 8/2002 | Barnett | 623/6.27 |
| 6,428,574 B1 | 8/2002 | Valunin et al. | 623/6.28 |
| 6,443,985 B1 | 9/2002 | Woods | 623/6.46 |
| 6,464,725 B2 | 10/2002 | Skotton | 623/6.34 |
| 6,478,821 B1 | 11/2002 | Laguette et al. | 623/6.49 |
| 6,485,516 B2 | 11/2002 | Boehm | 623/6.49 |
| 6,551,354 B1 | 4/2003 | Ghazizadeh et al. | 623/6.43 |
| 6,558,420 B2 | 5/2003 | Green | 623/6.34 |
| 6,616,691 B1 | 9/2003 | Tran | 623/6.11 |
| 6,616,692 B1 | 9/2003 | Glick et al. | 623/6.34 |
| 2002/0107568 A1 | 8/2002 | Zadno-Azizi et al. | 623/6.37 |
| 2002/0111678 A1 | 8/2002 | Zadno-Azizi et al. | 623/6.34 |
| 2002/0116057 A1 | 8/2002 | Ting et al. | 623/6.34 |
| 2002/0116058 A1 | 8/2002 | Zadno-Azizi et al. | 623/6.37 |
| 2002/0116059 A1 | 8/2002 | Zadno-Azizi et al. | 623/6.37 |
| 2002/0116060 A1 | 8/2002 | Nguyen et al. | 623/6.37 |
| 2002/0116061 A1 | 8/2002 | Zadno-Azizi et al. | 623/6.37 |
| 2002/0138141 A1 | 9/2002 | Zadno-Azizi et al. | 623/6.43 |
| 2002/0161434 A1 | 10/2002 | Laguette et al. | 623/6.16 |
| 2002/0173847 A1 | 11/2002 | Pham et al. | 623/6.26 |
| 2003/0018384 A1 | 1/2003 | Valyunin et al. | 623/6.34 |
| 2003/0060881 A1 | 3/2003 | Glick et al. | 623/6.37 |
| 2003/0074061 A1 | 4/2003 | Pham et al. | 623/6.34 |
| 2003/0078656 A1 | 4/2003 | Nguyen | 623/6.37 |
| 2003/0078657 A1 | 4/2003 | Zadno-Azizi et al. | 623/6.37 |
| 2003/0078658 A1 | 4/2003 | Zadno-Azizi | 623/6.37 |

FOREIGN PATENT DOCUMENTS

| | | |
|---|---|---|
| EP | 0 162 573 A2 | 11/1985 |
| EP | 0 328 117 A2 | 8/1989 |
| EP | 0 329 981 A1 * | 8/1989 |
| EP | 0 336 877 B1 | 10/1989 |
| EP | 0 337 390 A2 | 10/1989 |
| EP | 0 337 390 B1 | 10/1989 |
| EP | 0 359 539 B1 | 3/1990 |
| EP | 0 507 292 A1 | 10/1992 |
| EP | 0 507 292 B1 | 10/1992 |
| EP | 0 592 813 A1 | 4/1994 |
| JP | 2-126847 | 5/1990 |
| WO | WO 87/07208 | 12/1987 |
| WO | WO 96/16780 | 7/1996 |
| WO | WO 99/20206 | 4/1999 |
| WO | WO 00/66037 | 11/2000 |
| WO | WO 00/66040 | 11/2000 |
| WO | WO 01/34067 A1 | 5/2001 |
| WO | WO 02/071983 A1 | 9/2002 |
| WO | WO 03/000154 A2 | 1/2003 |
| WO | WO 03/000154 A3 | 1/2003 |

OTHER PUBLICATIONS

Schachar, Ann. Opthalmol., "Zonular Function: A New Hypothesis With Clincial Implications," Mar.-Apr. 1994; 26: 36-38.

Schachar, et al., Ann. Opthalmol., "Experimental Support for Schachar's Hypothesis of Accommodation," 1993; 25: 404-409.

Schachar, "Cause and Treatment of Presbyopia With a Method for Increasing the Amplitude of Accommodation", Ann. Opthalmol. 1992, 24:445-447, 452.

Hara et al., Accommodative Intraocular Lens with Spring Action Part 1: Design and Placement in an Excised Animal Eye, Opthalmic Surgery 1990 21(2): 128-133.

Koretz et al., "How the Human Eye Focuses", Sci. Amer., Jul. 1988, 259(1) 92-99.

Grinberg, "Questioning Our Classical Understanding of Accommodation and Presbyopia", Amer. J. Optometry & Physiological Optics, Jul. 1986, 63(7): 571-580.

* cited by examiner

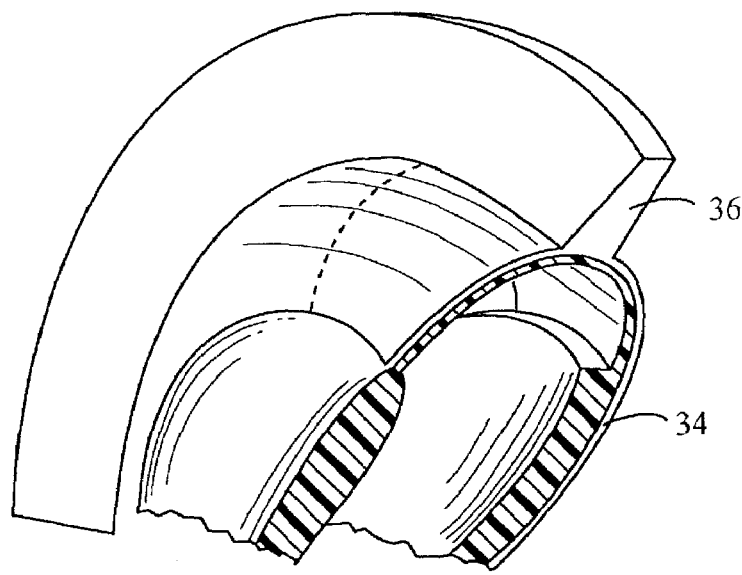
Figure 8
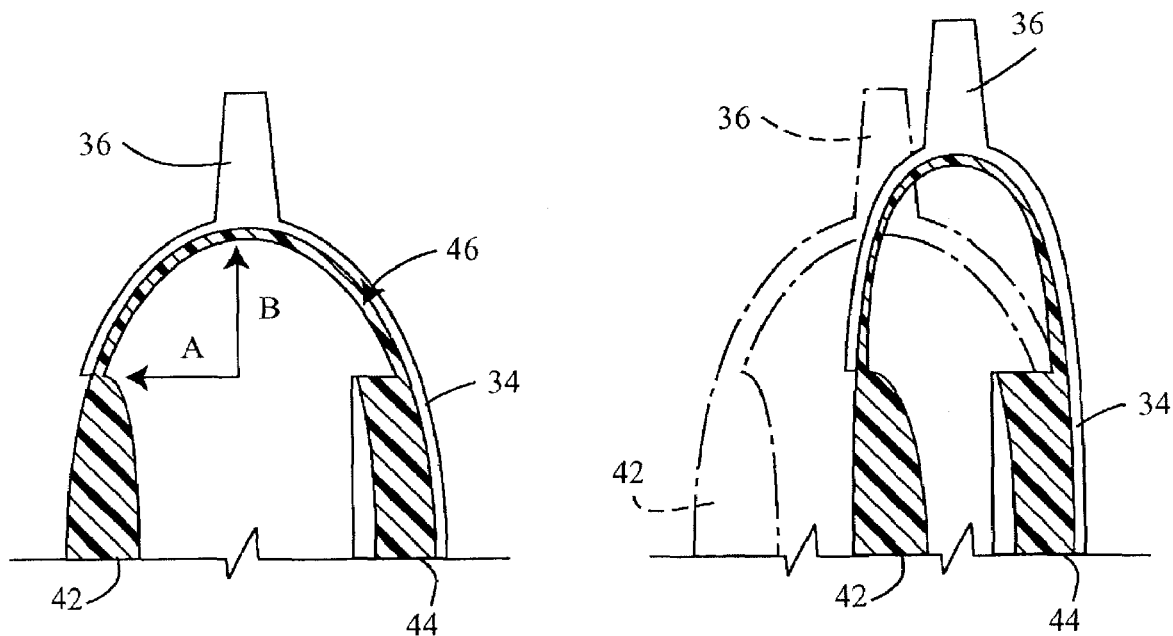
Figure 9
Figure 10

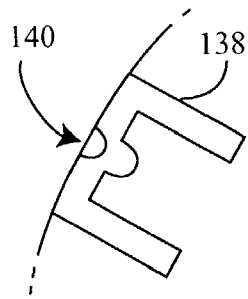
Figure 33
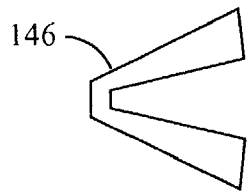
Figure 35
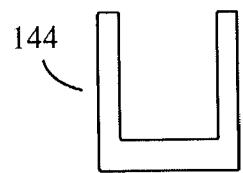
Figure 34
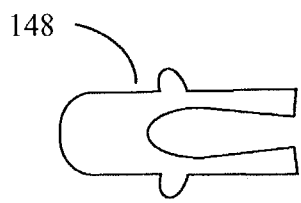
Figure 36
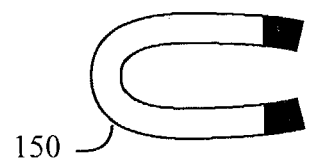
Figure 37
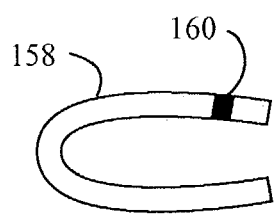
Figure 39A
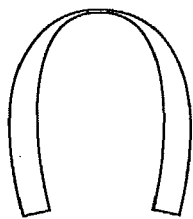
Figure 38
Figure 39B
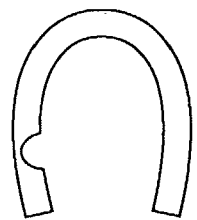
Figure 39C
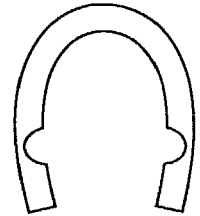
Figure 39D

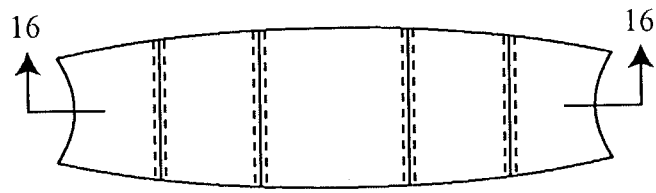
Figure 40B
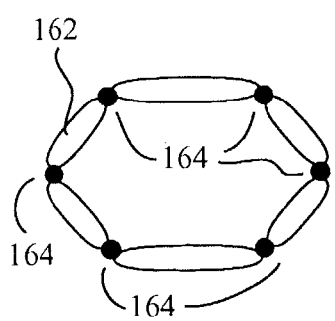
Figure 40C
Figure 40A
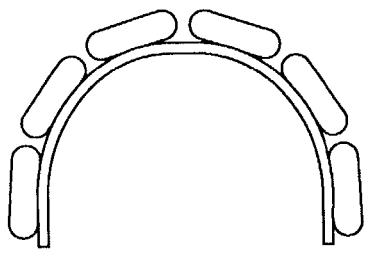
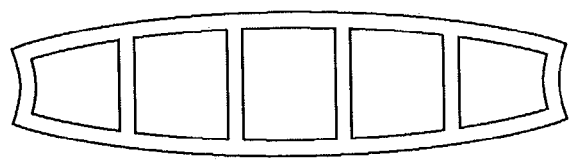
Figure 40D
Figure 40E
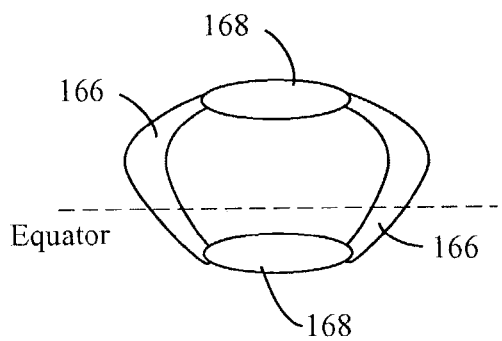
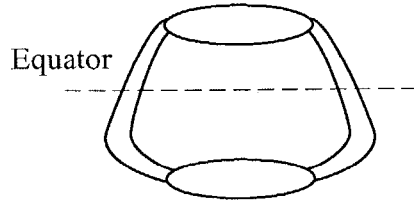
Figure 41A
Figure 41B

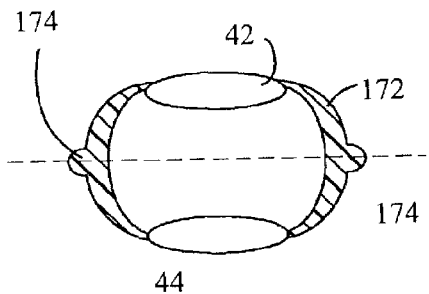
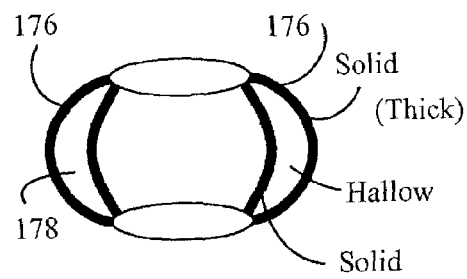
Figure 42
Figure 43A
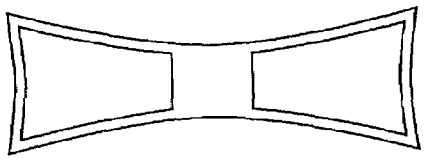
Figure 43C
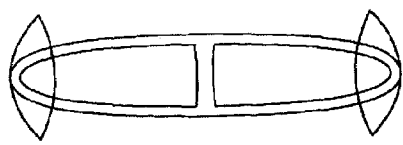
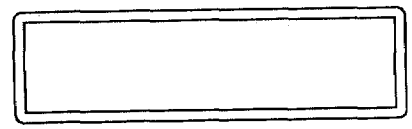
Figure 43B
Figure 43D
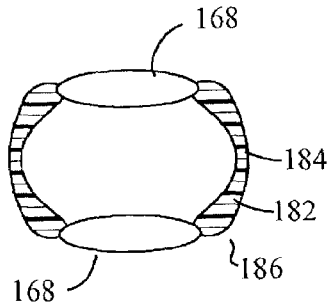
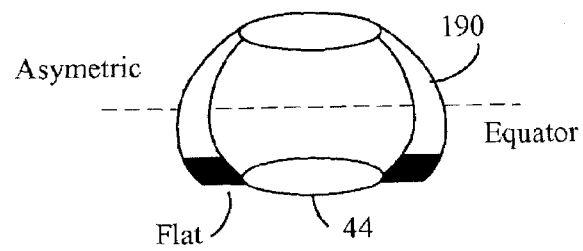
Figure 44
Figure 45A
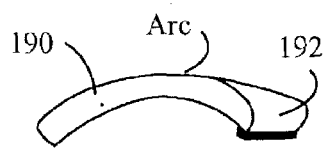
Figure 45B

HAPTICS FOR ACCOMMODATIVE INTRAOCULAR LENS SYSTEM

RELATED PATENT

This application is a continuation-in-part of U.S. patent application Ser. No. 09/288,560, entitled "Open Chamber, Elliptical Accommodative Intraocular Lens System" which was filed Apr. 9, 1999, and issued as U.S. Pat. No. 6,488,708 B2 on Dec. 3, 2002.

BACKGROUND OF TILE INVENTION

This invention relates to an improved elliptical, accommodative, intraocular lens system operable to be positioned within the interior of an evacuated capsular bag of a human eye. More specifically, this invention relates to an open elliptical, accommodative, intraocular lens method and apparatus operable to be inserted within an evacuated capsular bag of a human eye following extracapsular surgery to remove and replace a dysfunctional natural crystalline lens. The invention finds particular application in restoring bifocal vision following cataract surgery, correction of myopia, correction of presbyopia and treatment of the symptoms of retinal damage, such as, age related macular degeneration of the human eye.

In the human eye, multifocal vision is provided by a combination of a convex-concave lens, known as the cornea, positioned in front of the iris and a bi-convex lens position within a clear elliptical envelope behind the iris and in front of the vitreous humor of the eye. Accommodation of vision at both infinity and near vision of 250 mm is provided by a peripheral muscular body extending about the capsular bag and connected to the equator thereof by Zonula of Zinn which are thin strands attaching the equator of the capsular bag to the diary muscles. Tension and the relaxation of the ciliary muscles cause the capsular bag to lengthen or contract which varies the focus of the eye.

In certain instances at an early age, such as trauma or heredity, or in later stages of the life cycle, the natural crystalline lens of a human becomes cloudy and hardened, somewhat like milk glass, which occludes vision and results in eventual blindness. This condition is known as a cataract and was a major source of blindness in mankind for centuries. As early as 1766 Cassanova, in his memoirs, suggested that an intraocular lens could be implanted within a human to replace an opaque natural crystalline lens. It was not until 1949, however, that a Dr. Harold Ridley, at the Thomas Hospital in London, inserted the first intraocular lens within the eye of a woman of about 60 years of age following cataract extraction. Early IOLs, however, tended to dislocate, cause iris atrophy and in some instances secondary glaucoma. Attempts to overcome the early disadvantages of Dr. Ridley's solid posterior chamber lens included placement of a lens in the anterior chamber, in front of the iris. In addition Dr. Binkhorst of Holland invented an iris clip lens and Dr. Choyce an iris plane lens. However, both anterior chamber and iris fixed lenses created a risk of damages to delicate iris tissue.

An advanced in the intraocular lens art occurred when Dr. Shearing invented the first, practical, posterior chamber lens. Dr. Shearing's design included a bi-convex polymethylmethacrylate (PMMA) lens body which was positioned behind the iris and against the ciliary muscle or within the capsular bag. The Shearing IOL was maintained in a generally central axis of vision by thin strand haptics that extended radially from the peripheral edge of the lens optic and haptic were curved at their distal ends. The curved portions of the haptics abutted against peripheral tissue of the eye to support the lens. Although the Shearing lens haptics had small arc contact zones, the success of the lens lead other pioneers to develop a variety of haptic designs, such as, a C-loop or an S-loop and other designs to relieve trauma to adjacent contact tissue. A significant limitation of all fixed focus intraocular lens designs is that the focal point is fixed at infinity. Accordingly, for all near vision tasks, conventional reading glasses became necessary. In this connection, it is believed the several million pair of reading glasses are sold annually within the United States alone.

In addition to the incidences of cataract formation and its attendant tendency to blindness, reductions in both amplitude and speed of accommodation with age are well known. This condition is known as presbyopia. The amplitude of accommodation decreases progressively with age from some 14 diopters in a child of ten years to near zero at age 52. The exact explanation for the physiological phenomena is not well documented, however, it is observed that the curvatures of excised senile lenses were considerably less than those of juvenile ones. This failure could be due to a hardening of the lens material, sclerosis, decrease in modules of elasticity, or to a decrease in thickness of the capsule or a combination of the above. Regardless of the cause, it is a recognized fact that beginning at about age 40-45 correction for both near and far vision becomes necessary in most humans. Conventional techniques include bifocal glasses, bifocal contact lens, contact lenses for distance and reading glasses for near vision, and mono-focus contact lens sets where one eye carries a contact lens for distance vision and the other eye carries a contact lens for reading. Still further refractive surgery for distance vision coupled with reading glasses has been used successfully to correct presbyopia. Notwithstanding the grateful relief of being able to see clearly at both near and distance, all of the above solutions are compromises, in one form or another, and are dramatically more inconvenient than the natural bifocal vision of youth.

A somewhat related visual dysfunction in youth and young adults is mild to severe myopia or the loss of an ability to clearly focus at distance. Glasses, contact lenses or refractive surgery are the most common forms of accommodation, however, with certain cases of myopia it may be necessary to correct vision up to 30 to 40 diopters. As the degree of myopia increases the use of conventional solutions becomes less attractive and it would be highly desirable to be able to reliably correct this patient concern.

Still further, as humans age, or through viral inflammations or trauma, deterioration in retinal cells, including macular degeneration, can cause a dramatic loss of perception of light and color by rods and cones of the retina. In certain instances a degree of relief for humans suffering from impairment of vision from the loss of retinal cells can be achieved by increasing the intensity or magnification of images presented to healthy cells. In certain instances of macular degeneration it would be desirable to present a patient with an option of a correction of 30 to 70 diopters. This magnitude of correction is not readily achievable with presently known techniques.

The limitations to vision outlined in the proceeding are not intended to be exhaustive but are major concerns and represent limitations placed on mankind of impaired vision occasioned from trauma, disease, and/or age. It would be highly desirable if these limitations could be addressed and minimized or eliminated and thus restore to patients at least a portion of the accommodation and clarity of the vision of their youth.

SUMMARY OF THE INVENTION

In at least one preferred embodiment of the invention intended to accomplish the above, and other, objects of the invention are achieved by an open chamber, accommodative, intraocular lens system operable to be positioned within the interior of an evacuated capsular bag of a human eye. The present invention makes advances in the haptic cross-sections, novel complex lens structures including the introduction of the concept of a lens ledge, fixation of haptics to a lens ledge that makes possible the placement of a lens system into only a portion of the capsular bag, structural solutions to the lens itself in the form of removal of lens material to convert a lens portion into a structural support portion in order to provide customized fitted correction, and accordion structural solutions to ease the insertion of complex lenses into the capsular bag of the eye.

In general, the inventive intraocular lens system includes a first anterior lens optic and a second posterior lens optic which are arranged in axial alignment visually. An open chamber, haptic system is connected between the two lenses and in a preferred form three haptics segments are fashioned in the form of elliptical or other shaped segments which are connected at their ends to the peripheral rims of the lens bodies and arc outwardly away from the visual axis of the lenses.

One embodiment of the present invention employs elliptical haptic cross-sectional elements which flex as the capsular bag is peripherally pulled outwardly at its equator and as the bag contracts. This contraction is produced by a patient's natural vision accommodative by the ciliary muscles of the eye. In this, the anterior lens is moved axially toward the posterior lens to provide vision at infinity. As the ciliary muscles are constricted and move radially inward, for near vision accommodation, tension on connective zonuals decreases and the patient's capsular bag thickens allowing the haptics to assume their natural memory state. However, the present invention also discloses additional embodiments wherein other cross-sections haptic elements are employed.

Although the use of a two optic lens system is preferred, wherein the anterior lens is bi-convex and the posterior lens is a negative lens, such as a concavo-convex lens, to provide improved nesting of lenses to facilitate insertion into the capsular bag, and further to provide a corrective range of accommodation of about 4 diopters following extracapsular cataract surgery, other lens embodiments are contemplated by the subject invention. In this, other lens cross-sectional configurations can be used such as for example, concavo-planar or concavo-convex for either the anterior of posterior lens. In still other instances it may be desirable to remove the posterior lens entirely or eliminate its optic function by using a biplanar lens body. Finally, the invention also envisions adding more than two lenses, such as three lenses, in instances where extreme dioptive correction is desirable.

In one embodiment, three elliptical haptic segments are used extending at an arc of about 40 degrees outwardly from the rims of the lens optics and are peripherally spaced around the periphery with 80 degree segments of open space. These haptic segments are elliptical in cross-section and are fashioned in a natural state to have an elliptical ratio of 0.96. Other arrangements of the haptics are also envisioned such as two wider based haptics or four or more haptics that would be thinner in outer width. The underlying criteria is that the haptics are flexible enough to enable relatively unrestricted movement of the anterior lens toward the posterior chamber lens of about 1.9 mm or so in response to the natural movement of the ciliary muscle and zonula attached to the capsular bag while simultaneously being stiff enough to support the lens or lenses of the optic system in visual axial alignment within the capsular bag of a patient's eye.

In another embodiment, various additional haptic cross-sectional areas are provided, which areas are designed to increase the pressure applied to the capsular bag through the use of pressure points, or designed to decrease the pressure applied to the capsular bag by a hinge design to improve patient vision by reducing the amount of effort required for patient focus.

In yet other embodiments, the concept of a ledge structure is introduced to lenses which then provide the ability to provide specific fixation of haptics to lenses in ways that permit customized placement of the lens system in the eye—the lens system of the present invention no longer requires that the lenses be located in the customary location according to the prior art. As a result, it is now possible to provide customized and fitted correction.

The present invention further introduces the concept of an accordion-shaped haptic connection is introduced between stacked lenses to ease the insertion of complex lenses into the capsular bag of the eye.

Another concept introduced by the present invention is specific formation of structural support by the lens itself, by using only the active portion of a lens, removing material from the lens to form structural support for the lens from the lens material itself.

Other concepts introduced by the present invention will become apparent as set forth below.

BRIEF DESCRIPTION OF THE DRAWINGS

Other object and advantages of the present invention will become apparent from the following detailed description of preferred embodiments of the invention taken in conjunction with the accompanying drawings wherein:

FIG. 8 is a schematic and axonometric illustration of an open chamber, elliptical, accommodative intraocular lens segment in accordance with a preferred embodiment of the invention positioned within the capsular bag of a human eye;

FIG. 9 is a partial schematic side view of the accommodative, intraocular lens system, depicted in FIG. 8, in accordance with the invention which discloses the longitudinal elliptical configuration of a haptic of the lens system;

FIG. 10 is a schematic illustration of the motion of the open chamber, elliptical, accommodative, intraocular lens system in accordance with a preferred embodiment of the invention, depicted in FIGS. 8 and 9, wherein phantom lines represent a segment of the lens in a natural memory condition following insertion into the capsular bag of a patient's eye, with the patient's ciliary muscle constricted inward to accommodate for near vision, and the solid line segment depicts the position of the lens system when the patient's ciliary muscle relaxes and peripherally expands and stretches the capsular bag outward narrowing the distance between the lens optics to provide accommodative vision at infinity;

FIG. 33 is a side view of a haptic that provides an external pressure relief region, a notch, for relieving pressure on the capsular bag of an eye when the haptic is placed in contact with the capsular bag as another embodiment of the present invention.

FIG. 34 is a side view of a squared-U shaped haptic as another embodiment of the present invention.

FIG. 35 is a side view of a squared-V shaped haptic as another embodiment of the present invention.

FIG. 36 is a side view of a haptic with multiple projections to prevent cell growth as another embodiment of the present invention.

FIG. 37 is a side view of a horseshoe-shaped haptic as another embodiment of the present invention, wherein a hinge is formed by partial removal of material at the end of the haptic, where the haptic attaches to the optic, to alter the movement of the optics relative to the haptic.

FIG. 38 is a side view of a modified, squared-V shaped haptic as another embodiment of the present invention, wherein a hinge is formed at the end of the haptic.

FIG. 39A is a side view of a horseshoe-shaped haptic that is provided with a hinged section as another embodiment of the present invention.

FIG. 39B is a side view of another horseshoe-shaped haptic that is provided with a hinged section at the arch as another embodiment of the present invention.

FIG. 39C is a side view of another horseshoe-shaped haptic that is provided with a single hinged section as another embodiment of the present invention.

FIG. 39D is a side view of another horseshoe-shaped haptic that is provided with two hinged sections as another embodiment of the present invention.

FIG. 40A is a side view of a haptic that is provided with multiple hinges as another embodiment of the present invention.

FIG. 40B is a plan view of a haptic that is provided with multiple bending areas.

FIG. 40C is a cross-sectional view taken along line 16-16 of FIG. 40B.

FIG. 40D is a is a side view of a haptic with multiple hinged areas, as another embodiment of the present invention.

FIG. 40E is a plan view of a haptic having a plurality of hinges according to another embodiment of the present invention.

FIG. 41A is a side view of a symmetrical haptics used in an intraocular lens system as another embodiment of the present invention.

FIG. 41B is a side view of an asymmetrical haptics used in an intraocular lens system as another embodiment of the present invention.

FIG. 42 is a side view of another embodiment where the longitudinal thickness of the haptic is varied, with dual external pressure projections to assert pressure points on the capsular bag.

FIG. 43A is a side view of another embodiment where the longitudinal thickness of the haptic is constant, but the lateral thickness of the haptic is varied (here laterally thickness is zero due to hollow haptic portions).

FIG. 43B is a longitudinal side view of an oval haptic of another embodiment of the present invention where the thickness is varied to provide multiple hollow portions.

FIG. 43C is a longitudinal side view of an angular haptic of another embodiment of the present invention where the thickness is varied to provide multiple hollow portions.

FIG. 43D is a longitudinal side view of a square haptic of another embodiment of the present invention where the thickness is varied to provide a hollow portion.

FIG. 44 is a side view of another embodiment of the present invention where the variation in longitudinal thickness of the haptics shows a thinner portion at the equator, and a thinker portion near the lenses.

FIG. 45A is a side view of an intraocular lens system with an arc-shaped haptic of another embodiment of the present invention wherein the haptic has a flat profile.

FIG. 45B is a perspective view of the haptic in FIG. 45A, wherein the haptic has a flat surface.

DETAILED DESCRIPTION OF PREFERRED EMBODIMENTS OF THE INVENTION

Turning now to the drawings wherein like numerals indicate like parts, there will be seen preferred embodiments of the invention. Before describing the preferred embodiment, however, a brief statement about the context of the invention is believed appropriate.

Context of the Invention

Figure 1:
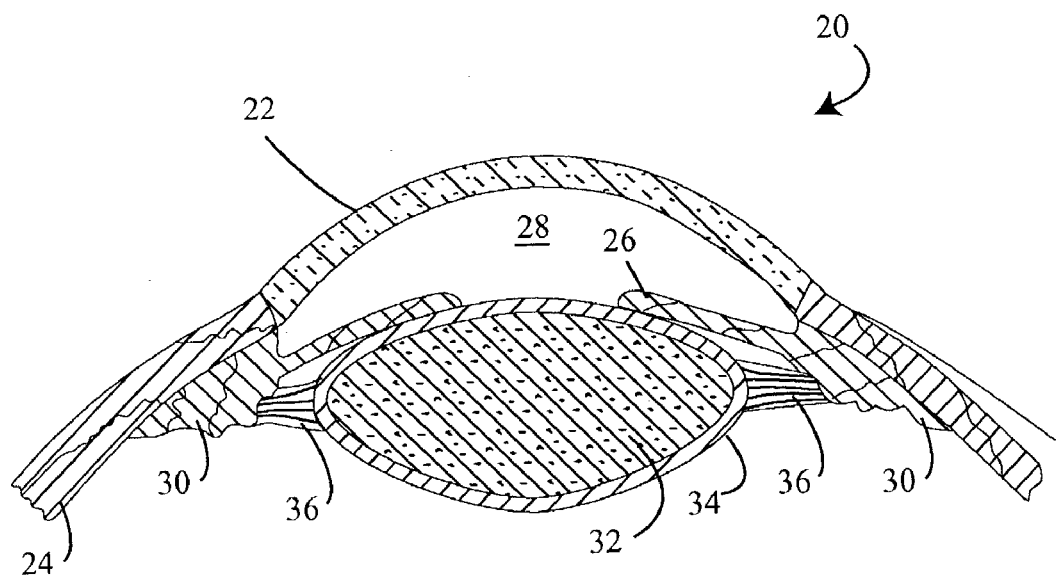
FIG. 1 a partial cross-sectional view of a human eye including a lens system composed of a convex-concave cornea and an accommodative, bi-convex natural crystalline lens positioned within a posterior chamber capsular bag.

Turning now to FIG. 1 there will be seen a partial cross-sectional view of an anterior segment of a human eye 20. Vision in humans is provided by a first convex/concave lens known as a cornea 22. This segment is partially spherical and is transparent to light. The cornea 22 is connected at its perimeter to a generally spherical exterior body of the eye known as a sclera 24. An iris 26 is positioned within an anterior chamber of the eye 28 and serves to vary the amount of light permitted to pass into the eye structure. The iris 26 extends into and is joined with a muscular structure known as the ciliary body or muscle 30 which extends peripherally about an interior portion of the eye. A natural crystalline lens 32 is positioned behind the iris 26 and is enrobed by a capsular membrane or bag 34. The natural crystalline lens 32 approximates an ellipse in cross-section and is circular when viewed along a line of sight. Zonula of Zinn 36 extend between the ciliary muscle 30 and an equator position of the capsular bag 34. A hyloid face, not shown, extends across the posterior surface of the lens 32 and isolates the forward segment of the eye from a vitreous chamber filled with clear vitreous humor.

Light is focused by the human eye by being refracted through the cornea and then refracted again through the bi-convex natural crystalline lens and is focused on a retina at the base of the eye. Bifocal vision from infinity to 250 millimeters is accommodated by varying the shape of the natural crystalline lens 32. More specifically, images at infinity are focused by the ciliary muscle 30 relaxing which permits their peripheral expansion and thus tensioning the zonula 36. Tension of the zonula draws the equator of the capsular bag radially outward and foreshortens the thickness of the lens body 32, providing for distance vision. In contrast, near vision is accommodated in a human eye by the ciliary muscles contracting which releases tension on the zonula allowing the lens body 32 to thicken into its natural state and thus focusing near objects upon the retina for transmission to the brain by the optic nerve.

A human eye adapts readily to variations in focal length and seamlessly enables a human to view objects at infinity as well as near vision instantly without conscious accommodation. Notwithstanding the perfect vision enjoyed by a majority of the population, an inability to view objects at infinity, or myopia, is frequently' encountered. This visual impairment can be corrected by refractive lens held by glasses, wearing contact lens or refractive surgery. In addition, certain humans do not focus near vision well. This is known as hyperopia and their vision can also be corrected by conventional refractive techniques. In certain instance of severe lack of accommodation these conventional procedures become undesirable and alternative procedures are needed.

Although a youth of ten years in age has an ability to change the dioptic power by fourteen diopters, this ability gradually decreases with age and by fifty or so the ability of the human eye to accommodate variation in focal length becomes essentially zero. This condition is referred to by presbyopia and a patient often requires correction for both near vision and far vision. This can be achieved by wearing bifocal glasses or contacts or undergoing refractive surgery for distance and wearing glasses for reading purposes.

In addition to the foregoing more conventional limitations on 20/20 vision, in instances of juvenile disease, trauma, and more frequently through age, the natural crystalline lens 32 becomes rigid and opaque to the passage of light. This condition is referred to as a cataract which can be corrected by removal of the lens 32 by a number of techniques, however, the most commonly perform surgery is known as extracapsular extraction. In this procedure, an annular opening is fashioned about the anterior visual center of the lens, centered by the iris, and then emulsifying and aspirating the hardened lens material. At least one procedure for phacoemulsification, irrigation and aspiration is disclosed in a Shearing U.S. Pat. No. 5,154,696. Once the natural crystalline lens is removed a bi-convex, fixed focal length optic, of about six millimeters in diameter, is typically fitted into the capsular bag and held in position by radially extending haptics. Although cataract surgery and insertion of an intraocular lens is the most frequently performed surgical procedure in the United States, and has achieved a considerable degree of sophistication and success, an intraocular lens is selected with a diopter to achieve far vision and near vision must be corrected by wearing reading glasses.

Finally, retinal disease or damage can impair human vision and one form is known as macular degeneration which usually occurs with advance in age. The symptom of macular degeneration can be alleviated, to a degree, by providing high diopters in the 30 to 70 range such that the rods and cones available to receive sight are utilize to their fullest.

From the foregoing context it will be appreciated that improvements in the eye care industry can be made with respect to correction of vision such as myopia, hyperopia, presbyopia, replacement of bifocal vision following cataract extraction and treatment of retinal dysfunction such as macular degeneration.

Open Chamber, Elliptical, Accommodated, Intraocular Lens System

Figure 2:
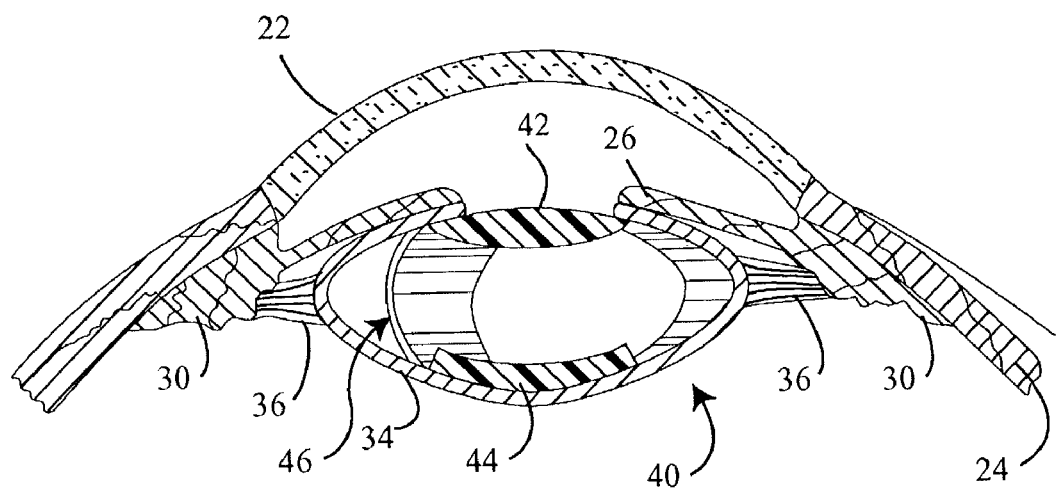
FIG. 2 is a partial cross-sectional view of a human eye as depicted in FIG. 1 where the natural crystalline lens has been replaced with an open chamber, accommodative, intraocular lens in accordance with one preferred embodiment of the invention to restore a patient's natural, accommodative, multifocal vision following extracapsular surgery.

Referring now to FIG. 2, the subject invention is directed to an open chamber, elliptical, accommodated, intraocular lens system 40 which is operable to correct and/or eliminate vision impairments of the type described above. The intraocular lens system 40 includes an anterior lens 42, a posterior lens 44 and haptic segments 46 operably connecting the anterior lens 42 with the posterior lens 44. As noted in FIG. 2, the subject intraocular lens system 40 is substantially elliptical in cross-section and operably conforms to the interior three-dimensional surface of the capsular bag 34.

Figure 3:
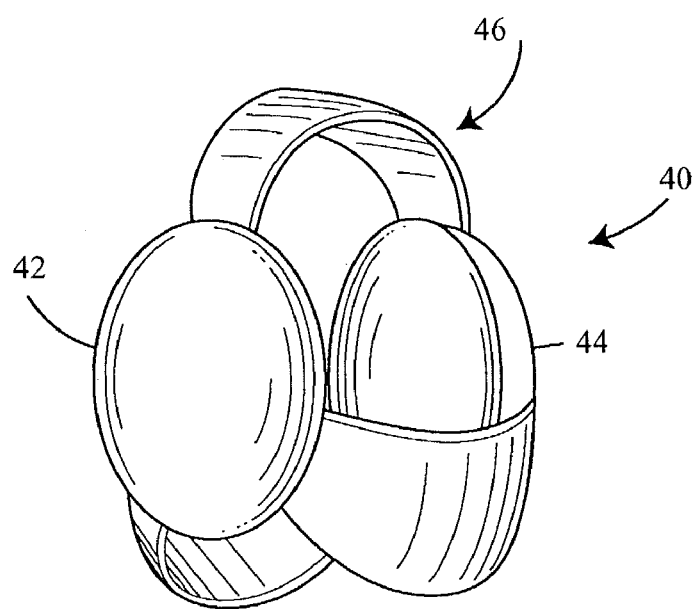
FIG. 3 (note sheet two) is and axonometric view of an open chamber, accommodative, intraocular lens having three elliptically shaped haptics extending between an anterior lens optic and a posterior lens optic in accordance with one preferred embodiment of the invention.
Figure 4:
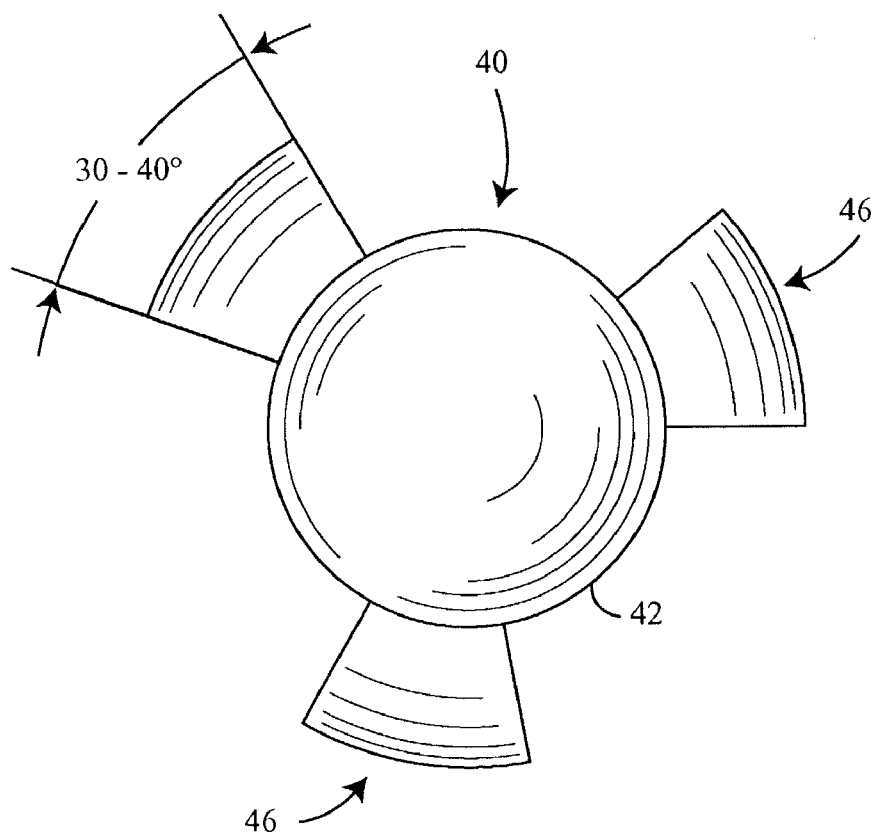
FIG. 4 is an end view of the open chamber intraocular lens system, as depicted in FIG. 3, and viewed along a visual axis as the lens is implanted within the capsular bag of a human eye.
Figure 5:
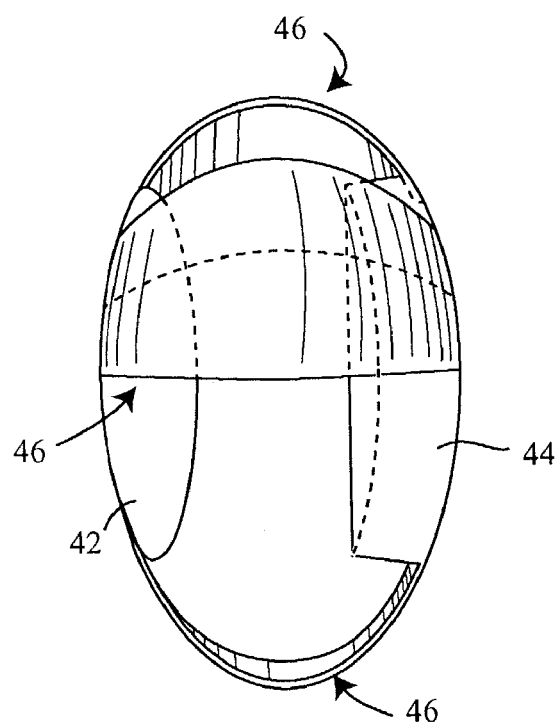
FIG. 5 is a side view of the intraocular lens system including a preferred form of three equally spaced haptic segments, as depicted in FIG. 4.

Turning to FIGS. 3-5 of the drawings, at sheet two, there is shown an axonometric view of the subject intraocular lens system 40, a front view, and a side view, respectively. The forward or anterior optic 42 is preferably bi-convex as depicted in FIG. 5 and has a diameter of approximately five millimeters for positioning within the capsular bag 34 immediately behind the iris 26. The power distribution of the anterior and posterior lenses may be varied to suit the needs of the particular patient, however, in a preferred embodiment the anterior lens is positive and the posterior lens is negative. The posterior lens 44 is in visually, axial alignment with the lens 42 and cooperates with the anterior lens to correct a wearer's vision. In a preferred embodiment, the lens 44 is fashioned in a spherical concavo-convex shape as depicted in FIGS. 3 and 5. Although in a preferred embodiment the anterior and posterior lens combinations are as stated above, other lens couples are contemplated by the subject invention including anterior lens fashioned with a concavo-planar, concavo-convex, and convex-concavo configurations. In a similar manner, the posterior lens may also exhibit the range of physical lens formation possibilities of being concave or convex or planar in order to achieve the desired visual result for a particular patient. Lenses are typically fabricated from an optical grade polymethyhnethacrylate (PMMA) however other materials may be utilized such as glass, silicone, or acrylics provided visual clarity, refractive ability, and bio-compatibility are all maintained.

Figure 6:
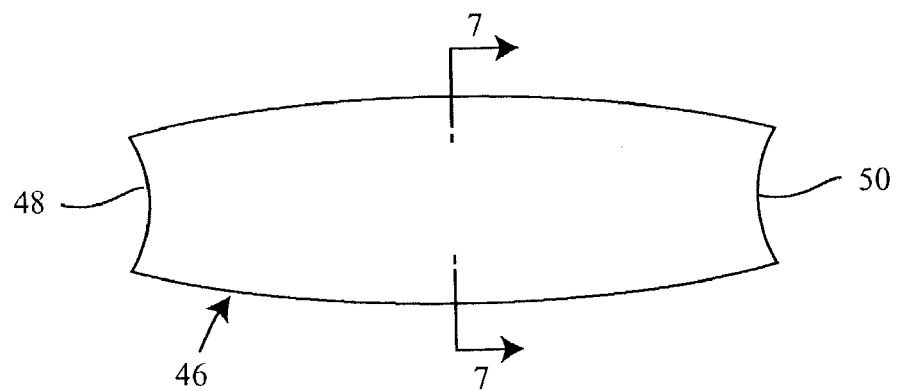
FIG. 6 (note sheet 3) is a plan view of a haptic component disclosing its preferred, general elliptical, configuration.
Figure 7:
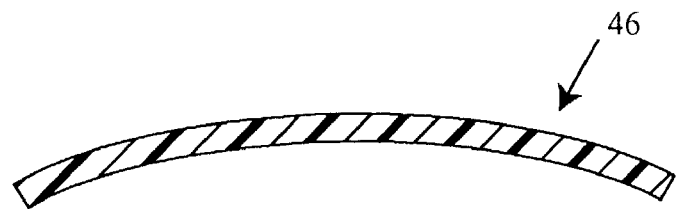
FIG. 7 is a cross-sectional view of the haptic component depicted in FIG. 6 and discloses the arcuate cross-sectional configuration of the haptic element.

In the subject invention, the anterior 42 and posterior 44 lenses are coupled together by a plurality of longitudinally elliptical haptics 46. The haptics are connected to the peripheral edges of the anterior and posterior lenses by stalking, integral formation, gluing, or other known techniques and are positioned on the peripheral edges of the lenses in equidistant peripheral locations. In a preferred embodiment, the haptics subtend an angle of thirty to forty degrees as viewed in a direction of line of sight, note FIG. 4, and extend outwardly approximately nine millimeters, in diameter, to approximate the normal internal diameter of the capsular bag of the human eye. As shown in FIG. 6, note sheet three, the haptic 46 is generally elliptical in a plan view and has arcuate end surfaces 48 and SO for attachment to the periphery of the anterior and posterior lenses as noted above. In cross-section, the haptics 46 are arcuate, note FIGS. 4 and 7, and have a radius of curvature of approximately 4.5 millimeters which enables the haptic to smoothly conform to the interior surface of an evacuated capsular bag.

The haptics 46 are preferably composed of polymethylmethacrylate S (PMMA) material which can be molded along with of the anterior or posterior lenses. In certain instances, it may be desirable to lessen the overall weight of the intraocular lens system within the interior of a patient's eye. In this instance the haptic 46 can be advantageously composed of a polypropylene material having a specific gravity of approximately 0.91 and thus the combination of the PMMA optics and polypropylene haptics offset and the lens system is approximately neutrally buoyant with the aqueous humor. In addition, the haptics can be advantageously composed of an acrylic having a water content of 2 to 30%, a hydroxyethyl-metbacrylate (HEMA), or polydimethylsiloxanes.

Although three radially extending haptics covering arcs of 30-40 degrees each, such as shown in FIGS. 3-5, constitute a preferred embodiment of the invention, other haptic arrangements of from two to five or more in number are envisioned and can be selected by those of ordinary skill in the art to satisfy the requirement of sufficient flexibility to provide the accommodated focusing of the lens system and simultaneous stiffness to maintain the axial position and orientation of the lens optics.

Turning to FIGS. 8-10, there will be seen schematic illustrations of a portion of the subject intraocular lens system positioned within a capsular bag 34 and particularly illustrated in FIG. 9 an elliptical cross-sectional configuration of the haptic 46 wherein the ratio provided by the height A of the ellipse over the length B is 0.96. It has been determined that this ratio is optimum for application of the ciliary muscles and zonula acting through the capsular bag to provide accommodative vision with the intraocular lens system 40. Although this configuration is preferred, it is envisioned that a more linear arrangement in the form of a triangle with rounded corners may be utilized to advantage provided the material, thickness and configuration remain both flexible and supportive.

Referring again to FIG. 8, a peripheral zone of zonula 36 is depicted which extends peripherally about and is connected to the capsular bag 34. In a condition when the ciliary muscle 30 is relaxed and retracted peripherally outwardly, the zonula 36 will be tensioned outwardly which will pull the equator of the capsular bag 34 into a configuration shown in solid lines in FIG. 10. This position of the capsular bag and the location of the anterior and posterior lenses is optimum for vision at infinity.

When the peripheral ciliary muscles 30 are constricted the hoop dimension is radially decreased which releases tension on the zonuals 36 and the capsular bag, biased by the natural shape of the intraocular lens system 40, assumes the condition indicated by phantom lines in FIG. 10. In this, the natural memory shape of the elliptical haptics 46 repositions the anterior lens 42 with respect to the posterior lens 44 axially and is the position used for focusing on near objects down to 250 millimeters. In a preferred embodiment, the subject intraocular lens system cooperates with the diary muscle, and zonula and capsular bag to permit a relative axial motion of the anterior lens with respect to the posterior lens of 1.9 millimeters and a power correction of 4 diopters. This accommodated motion of the subject intraocular lens system is achieved automatically, and seamlessly, within the human eye and thus is operable to permanently restore unaided binocular vision.

Although a preferred embodiment of the subject accommodative intraocular lens system has been disclosed and discussed in connection with FIGS. 3-8, other preferred embodiments exist with respect to specific applications such as disclosed in FIGS. 11-14. In this, FIGS. 11 and 12 disclose elliptical haptic, intraocular lens systems utilizing a single anterior lens body 52 which may be used to advantage for the correction of mild to severe myopia (nearsightedness) or hyperopia (farsightedness). In this embodiment, a plurality of elliptical haptics 54 connect at a first end to a peripheral portion of the first optic 52 and at a second end to a stabilizing ring 56 positioned in a location posterior to and in axial alignment to the optic 52. This embodiment is operably received within an evacuated capsular bag in a secure and stable manner similar to that shown in FIG. 2.

Figure 12:
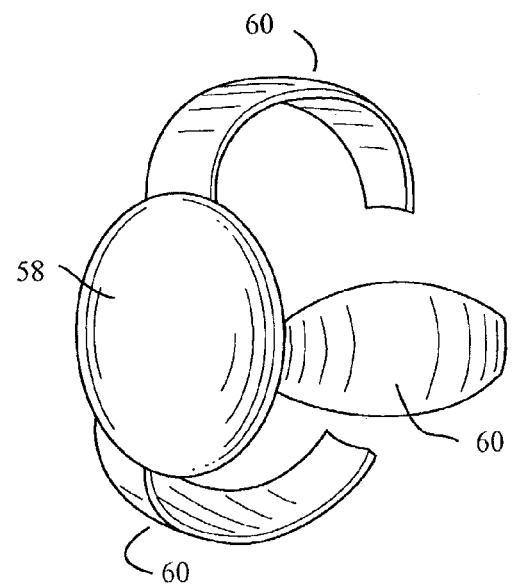
FIG. 12 is an illustration of another preferred form of the invention 5 having only one anterior positioned lens optic.

In an alternative embodiment of the invention a single lens optic 58, as depicted in FIG. 12, is supported by elliptical haptics 60 having a first end connected to a peripheral rim of the optic and extend to free end positions to a location of posterior proximity. This lens will also snuggly and accommodatively fit within an evacuated capsular bag for use in correction of myopia and hyperopia.

Figure 11:
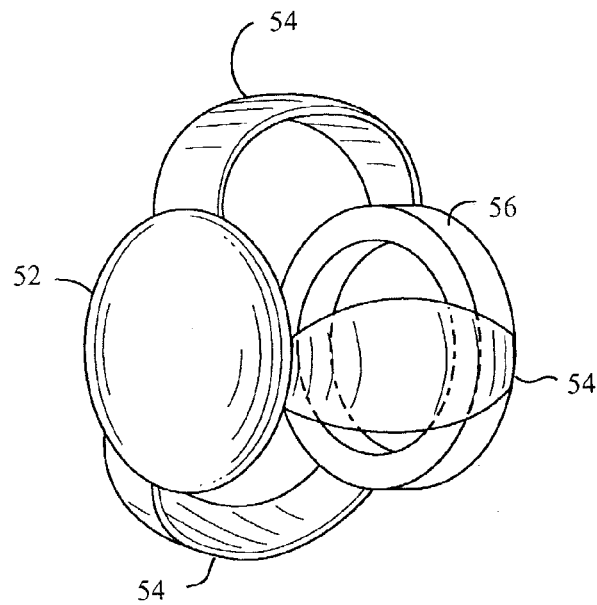
FIG. 11 (note sheet four) is an illustration of another preferred form of the invention where the open chamber, elliptical, accommodative intraocular lens system includes only one anterior positioned lens optic.

The cross-sectional configuration of the corrective lens 52 and 58, of the embodiments depicted in FIGS. 11 and 12, may be selected for the designated refractive purposes but it is preferred that the lens exhibit a concave-convex, piano-convex, or convex-piano surface configurations as viewed in cross-section.

Figure 13:
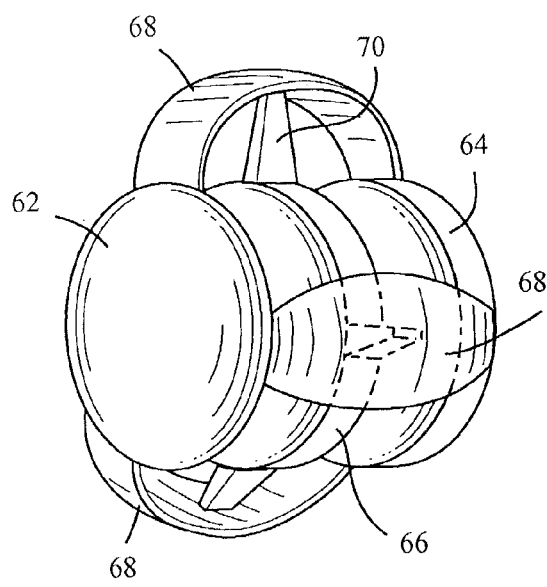
FIG. 13 is an axonometric illustration of another preferred embodiment of the invention where the intraocular lens system includes three lens optics in axial alignment.
Figure 14:
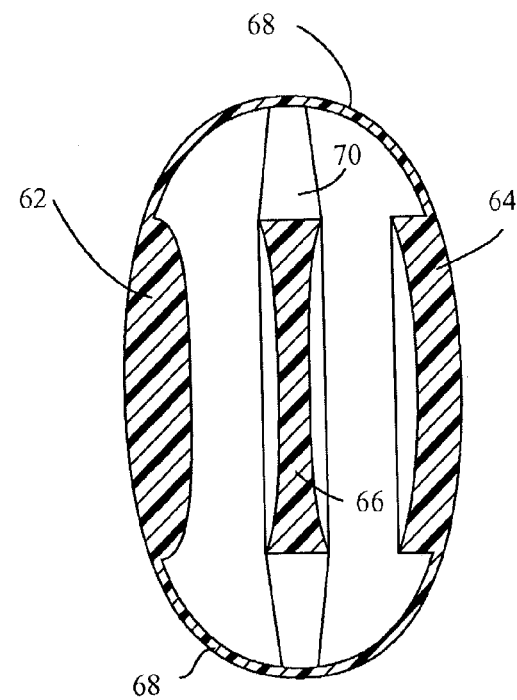
FIG. 14 is a cross-sectional view of a three lens optic system as illustrated in FIG. 13.

In certain instances such as macular degeneration it may be desirable to provide an accommodative intraocular lens system wherein the lens is capable of providing hyper-visual corrections of 30-70 diopters. Turning to FIGS. 13 and 14, there is shown an accommodative intraocular lens system including an anterior lens 62, a posterior lens 64, and an intermediate lens 66. An elliptical haptic system 68 surrounds and supports the anterior and posterior lenses of the lens system in a manner as previously described. The intermediate lens 66 is supported by radially extending arms 70 which project between the peripheral surface of the interior lens and the intermediate surface of the elliptical haptic 68. This support is illustrated particularly in FIG. 14 which discloses a schematic cross-sectional view taken along section lines taken through the center of adjacent haptics 68 in FIG. 13. The shape and dioptive power of each of the lens 62, 64, and 66 can be varied to suit a particular patient's circumstances. In this embodiment, the anterior lens is the principal moving lens during accommodation, the intermediate lens remains essentially axially stationary, as the support members 70 elongate, with movement of the zonula, and the posterior lens may move a small degree but less than the anterior lens 62. The power distribution of each of the lens may be varied to suit the needs of a specific patient. However, if a total power of 28 diopters is required an envisioned distribution would be eight dipoters for the anterior lens, ten diopters for the intermediate lens, and four dipoters for the posterior lens. Alternatively, the anterior lens may be employed that is four dipoters, the intermediate lens may be employed at four dipoters, and the posterior lens may be employed at twenty diopters.

Without attempting to set forth all of the desirable features of the subject invention an accommodative intraocular lens system including an anterior lens and posterior lens coupled with longitudinally, elliptical haptics operably serve to replace a natural crystalline lens within a patient's evacuated capsular bag and provide an accommodation of four or more diopters suitable to restore bifocal vision to most patient's following cataract surgery.

A single, anterior lens embodiment of the invention is advantageously operable to correct both myopia and hyperopia and single or dual lens designs find use in providing full accommodative restoration of vision to presbyopic patients.

In instances of retinal damage or degeneration, where high diopter powers enhance vision, a three lens embodiment of the invention can be used to produce magnification up to seventy diopters or more.

The elliptical ratio of 0.96 provides a particularly advantageous degree of rigidity and flexibility such that a patient's ciliary muscles, zonula, and natural capsular bag are able to restore a patient's accommodative vision without using other vision correcting devices.

Figure 15:
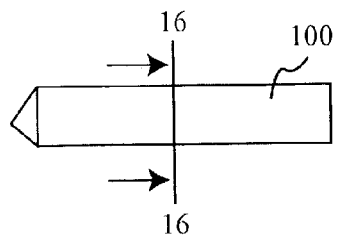
FIG. 15 is a perspective view of view of a haptic component of another embodiment of the present invention.
Figure 16:
FIG. 16 is a cross-sectional view of the haptic component depicted in FIG. 15 and discloses the triangular cross-sectional configuration of the haptic element.

FIG. 15 is a perspective view of view of a triangular haptic component 100 of another embodiment of the present invention. FIG. 16 illustrates a cross-sectional view of triangular haptic component 100 taken along line 16-16 of FIG. 15. As shown here, triangular haptic component 100 has a triangular cross-sectional area 102.

Figure 17:
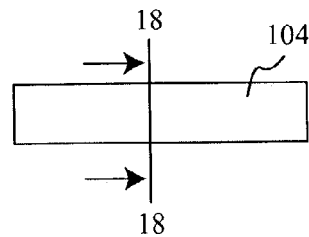
FIG. 17 is a perspective view of a haptic component of another embodiment of the present invention.
Figure 18:
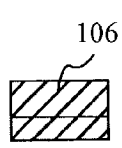
FIG. 18 is a cross-sectional view of the haptic component depicted in FIG. 17 and discloses the square cross-sectional configuration of the haptic element.

FIG. 17 is a perspective view of view of a square haptic component 104 of another embodiment of the present invention. FIG. 18 illustrates a cross-sectional view of square haptic component 104 taken along line 18-18 of FIG. 17. As shown, square haptic component 104 has a square cross-sectional area 106.

Figure 19:
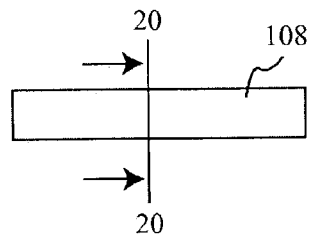
FIG. 19 is a perspective view of view of a haptic component of another embodiment of the present invention.
Figure 20:
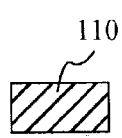
FIG. 20 is a cross-sectional view of the haptic component depicted in FIG. 19 and discloses the rectangular cross-sectional configuration of the haptic element.

FIG. 19 is a perspective view of view of a rectangular haptic component 108 of another embodiment of the present invention. FIG. 20 illustrates a cross-sectional view of rectangular haptic component 110 taken along line 20-20 of FIG. 19. As shown, square haptic component 104 has a square cross-sectional area 106.

Figure 21:
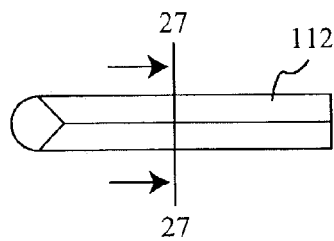
FIG. 21 is a perspective view of view of a haptic component of another embodiment of the present invention.
Figure 22:
FIG. 22 is a cross-sectional view of the haptic component depicted in FIG. 21 and discloses the arcuate pointed cross-sectional configuration of the haptic element.

FIG. 21 is a perspective view of view of an arcuate pointed haptic component 112 of another embodiment of the present invention. FIG. 22 illustrates a cross-sectional view of arcuate pointed haptic component 112 taken along line 22-22 of FIG. 21. As shown, arcuate pointed haptic component 112 has a square cross-sectional area 114.

Figure 23:
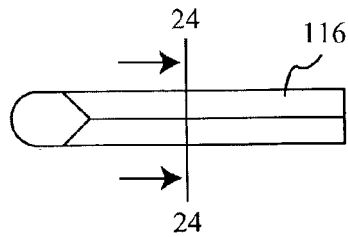
FIG. 23 is a perspective view of view of a haptic component of another embodiment of the present invention.
Figure 24:
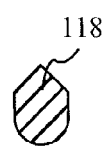
FIG. 24 is a cross-sectional view of the haptic component depicted in FIG. 23 and discloses the elongated arcuate pointed cross-sectional configuration of the haptic element.

FIG. 23 is a perspective view of view of an elongated arcuate pointed haptic component 116 of another embodiment of the present invention. FIG. 24 illustrates a cross-sectional view of elongated arcuate pointed haptic component 116 taken along line 24-24 of FIG. 23. As shown, elongated arcuate pointed haptic component 116 has a square cross-sectional area 118.

Figure 25:
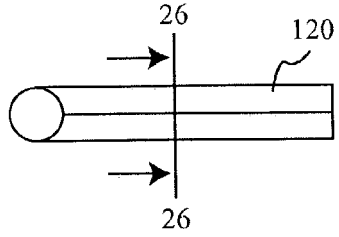
FIG. 25 is a perspective view of view of a haptic component of another embodiment of the present invention.
Figure 26:
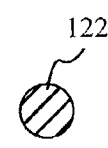
FIG. 26 is a cross-sectional view of the haptic component depicted in FIG. 25 and discloses the circular cross-sectional configuration of the haptic element.

FIG. 25 is a perspective view of view of a circular haptic component 120 of another embodiment of the present invention. FIG. 26 illustrates a cross-sectional view of circular haptic component 120 taken along line 26-26 of FIG. 25. As shown, circular haptic component 120 has a circular cross-sectional area 122.

Figure 27:
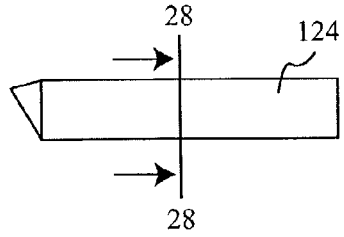
FIG. 27 is a perspective view of view of a haptic component of another embodiment of the present invention.
Figure 28:
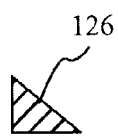
FIG. 28 is a cross-sectional view of the haptic component depicted in FIG. 27 and discloses the right triangle cross-sectional configuration of the haptic element wherein the outside corner closest to the capsular bag is sharp.

FIG. 27 is a perspective view of view of a first right triangle haptic component 124 of another embodiment of the present invention. FIG. 28 illustrates a cross-sectional view of first right triangle haptic component 124 taken along line 28-28 of FIG. 27. As shown, first right triangle haptic component 124 has a right triangle cross-sectional area 126.

Figure 29:
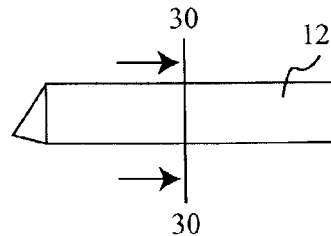
FIG. 29 is a perspective view of view of a haptic component of another embodiment of the present invention.
Figure 30:
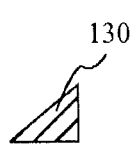
FIG. 30 is a cross-sectional view of the haptic component depicted in FIG. 29 and discloses another right triangle cross-sectional configuration of the haptic element wherein the inside corner farthest from the capsular bag is sharp.

FIG. 29 is a perspective view of view of a second right triangle haptic component 128 of another embodiment of the present invention. FIG. 30 illustrates a cross-sectional view of second right triangle haptic component 128 taken along line 30-30 of FIG. 29. As shown, second right triangle haptic component 130 has a right triangle cross-sectional area 130.

It can be seen that first right triangle haptic component 124 is opposite in orientation from that of second right triangle haptic component 128, depending on the type of correction needed by the patient.

Thus, from FIGS. 15-30, it can be seen that the haptic component may assume a variety of cross-sectional geometries. These geometries may be used to provide varying degrees of structural support to a lens, to provide a varying result in both the resting position of the lens in the capsular bag, as well as a varying result in the active position (muscle actuated position) of the lens in the capsular bag.

In all haptic components described in this specification, it will be appreciated that the component may be attached to any lens either "on top" of the lens, or "on the bottom" of the lens, depending on the type of results required in the resting and active position of the lens.

In addition, the present invention, in Figures below, introduces the concept of a variation in the thickness of a haptic, either longitudinally or laterally, or a variation in haptic external geometry (as opposed to internal, cross-sectional geometry), and the advantages and uses of such variations.

Figure 31A:
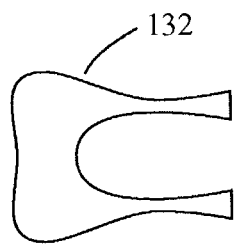
FIG. 31A is a side view of a haptic that illustrates variation in longitudinal thickness of another embodiment of the present invention.

FIG. 31A is a side view of a thickened haptic 132A that illustrates variation in longitudinal thickness of another embodiment of the present invention. On the right side, the haptic connection to a lens at each end, top and bottom, is not shown for clarity.

Figure 31B:
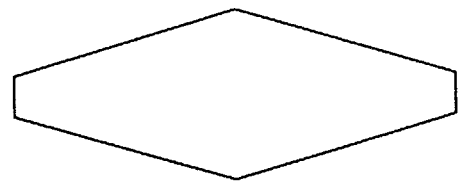
FIG. 31B is a side view of a haptic that illustrates variation in longitudinal thickness of another embodiment of the present invention.
Figure 31C:
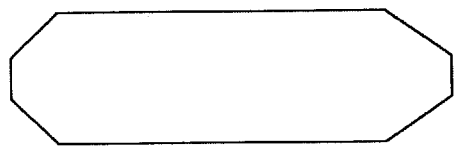
FIG. 31C is a side view of a haptic that illustrates variation in longitudinal thickness of another embodiment of the present invention.
Figure 31D:
FIG. 31D is a side view of a haptic that illustrates variation in longitudinal thickness of another embodiment of the present invention.

Similarly, FIGS. 31B, 31C and 31D are side views of haptics 132B, 132C, and 132D, respectively, that illustrate further variations in longitudinal thickness.

Figure 32A:
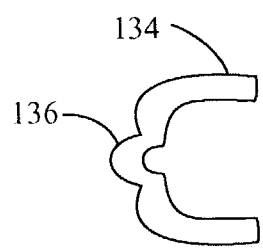
FIG. 32A is a side view of a haptic that provides an external pressure projection for engagement with the capsular bag of an eye as another embodiment of the present invention.

FIG. 32A is a side view of a pressure-projecting haptic 134. As seen, the variation in longitudinal thickness results in the formation of a pressure nodule 136 that provides an external pressure projection for engagement with the capsular bag of an eye as another embodiment of the present invention. Pressure nodule 136 serves to exert additional pressure on the capsular bag of an eye, thereby relieving the patient from straining to produce such pressure through muscle action. This is desirable in the case where a patient is nearsighted. Assisting the patient by removing the need for constant muscle exertion to achieve a normal focus also may produce the side benefit of relieving patient headaches and reducing the level of accommodation that is required.

Figure 32B:
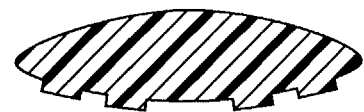
FIG. 32B is a longitudinal section view of a haptic of an alternative embodiment that provides a pressure match to expedite the ciliary muscle forces.

FIG. 32B is a longitudinal section view of a haptic that provides a pressure match at pressure points 135 to expedite the ciliary muscle forces.

Figure 32C:
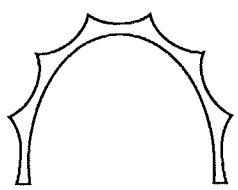
FIG. 32C is a side view of a haptic of an alternative embodiment that provides a plurality of pressure points 137.

FIG. 32C is a side view of a haptic that provides a plurality of pressure points 137.

FIG. 33 is a side view of a pressure-relieving haptic 138 that provides an external pressure relief region 140 for relieving pressure on the capsular bag of an eye when the haptic is placed in contact with the capsular bag as another embodiment of the present invention. This is desirable in the case where a patient is farsighted.

As the various geometries are explored below, the purpose of the various geometries is to achieve certain mechanical advantages within the capsular bag. These advantages may relate to fixing the default position of the lenses, fixing the active position of the lenses, providing mechanical advantage to the ciliary muscles, decreasing mechanical advantage to the ciliary muscles by utilizing stiffer haptic geometries that flex less, decreasing or increasing the focal length, and providing a customized fit to patients who do not have a standard distance between the capsular bag and the retina (either shorter or longer).

FIG. 34 is a side view of a squared-U shaped haptic 144 as another embodiment of the present invention.

FIG. 35 is a side view of a squared-V shaped haptic 146 as another embodiment of the present invention.

FIG. 36 is a side view of a haptic 148 with multiple projections to prevent cell growth as another embodiment of the present invention.

FIG. 37 is a side view of a horseshoe-shaped haptic 150 as another embodiment of the present invention.

FIG. 38 is a side view of a modified, squared-V shaped haptic 154 as another embodiment of the present invention.

FIG. 39A is a side view of a horseshoe-shaped haptic 158 that is provided with a hinged section 160 as another embodiment of the present invention. Hinged section 160 may be accomplished by providing a thinner cross-sectional area, resulting in a higher flexibility. Therefore, haptic 158 introduces the concept of combining a variation in external geometry together with variation in longitudinal thickness to achieve specific advantages.

FIG. 39B is a side view of another horseshoe-shaped haptic 158B that is provided with a hinged section 160B at the arch as another embodiment of the present invention. The hinged section 160B is accomplished by thinning the cross-sectional area, thereby providing a weaker area for bending.

FIG. 39C is a side view of another horseshoe-shaped haptic 158C that is provided with a single hinged section 160C as another embodiment of the present invention. Hinged section 160C is accomplished by removal of material to provide an area for bending.

FIG. 39D is a side view of another horseshoe-shaped haptic 158D that is provided with two hinged sections 160D as another embodiment of the present invention. Similar to the hinged section 160C in FIG. 39C, the two hinged sections 160D are created by removal of material to provide an area for bending.

FIG. 40A is a side view of a haptic 162A that is provided with multiple hinges 164A as another embodiment of the present invention.

FIG. 40B is a plan view of a haptic 162B that is provided with multiple bending areas 164B.

FIG. 40C is a cross-sectional view of haptic 162B taken along line 16-16 of FIG. 40B.

FIG. 40D is a is a side view of a haptic 162D with multiple hinged areas 164D, as another embodiment of the present invention.

FIG. 40E is a plan view of a haptic 162E having a plurality of hinges 164E according to another embodiment of the present invention.

FIG. 41A is a side view of symmetrical haptics used in an intraocular lens system as another embodiment of the present invention. It is important to note that the prior art, until the present time, worked to achieve an equator position of the capsular bag, wherein the equator position is equidistant from the lenses. However, the present invention employs the various geometries in a customized approach such that the lenses 168 are not equidistant from the equator.

FIG. 41B is a side view of an asymmetrical haptics used in an intraocular lens system as another embodiment of the present invention.

FIG. 42 is a side view of another embodiment where the longitudinal thickness of the haptic 172 is varied, with dual external pressure projections 174 to assert pressure points on the capsular bag.

FIG. 43A is a side view of another embodiment where the longitudinal thickness of the haptic 176A is constant, but the lateral thickness of the haptic is varied (here laterally thickness is zero due to hollow haptic portions).

FIG. 43B is a longitudinal side view of an oval haptic 176B of another embodiment of the present invention where the thickness is varied to provide multiple hollow portions 177C.

FIG. 43C is a longitudinal side view of an angular haptic 176C of another embodiment of the present invention where the thickness is varied to provide multiple hollow portions 177C.

FIG. 43D is a longitudinal side view of a square haptic 176D of another embodiment of the present invention where the thickness is varied to provide a hollow portion 177D.

FIG. 44 is a side view of another embodiment of the present invention where the variation in longitudinal thickness of the haptics 182 shows a thinner portion 184 at the equator, and a thinker portion 186 near the lenses 168.

FIGS. 45A-51 provide additional embodiments of the present invention relating to arc-shaped, or bent haptic geometries.

FIG. 45A is a side view of an intraocular lens system with an arc-shaped haptic 190 of another embodiment of the present invention wherein the haptic has a flat profile.

FIG. 45B is a perspective view of the haptic in FIG. 45A, wherein haptic 190 assumes an arced/arched geometry 192, and has a flat surface 194.

Figure 46A:
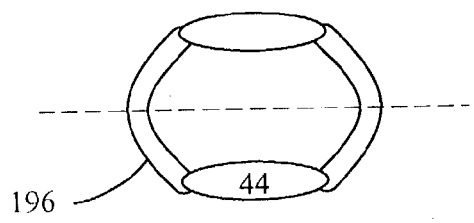
FIG. 46A is a side view of an intraocular lens system with an arc-shaped haptic of another embodiment of the present invention wherein the haptic has a complex profile including both flat and arc portions.
Figure 46B:
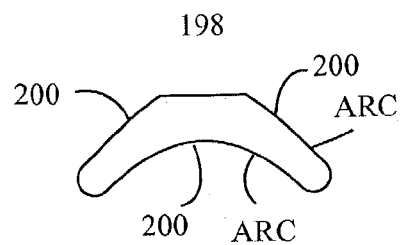
FIG. 46B is a side view of the haptic in FIG. 46A.

FIG. 46A is a side view of an intraocular lens system with an arc-shaped haptic 196 of another embodiment of the present invention, and FIG. 46B is a side view of haptic 196, wherein the haptic 196 has a complex profile including both flat 198 and arc portions 200.

Figure 47A:
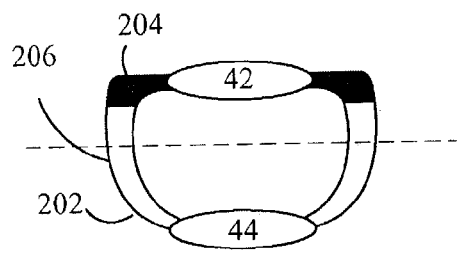
FIG. 47A is a side view of an intraocular lens system with an arc-shaped haptic of another embodiment of the present invention wherein the haptic has a complex profile including both flat and arc portions.
Figure 47B:
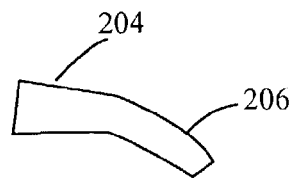
FIG. 47B is a side view of the haptic in FIG. 47A.

FIG. 47A is a side view of an intraocular lens system with an arc-shaped haptic 202 of another embodiment of the present invention, and FIG. 47B is a side view of the haptic 202 in FIG. 47A, wherein the haptic 202 has a complex profile including both flat 204 and arc 206 portions.

Figure 48:
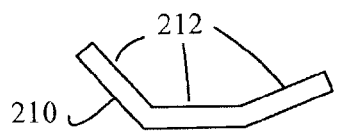
FIG. 48 is a side view of one embodiment of a bent haptic of the present invention.

FIG. 48 is a side view of one embodiment of a bent haptic 210 of the present invention comprising three segments 212 of equal length, joined together at bent angles.

Figure 49:
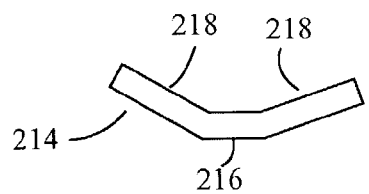
FIG. 49 is a side view of another embodiment of a bent haptic of the present invention.

FIG. 49 is a side view of another embodiment of a bent haptic 214 of the present invention, comprising three segments. There is one short segment 216. Two longer end segments 218 are joined to short segment 216 at an angle.

Figure 50:
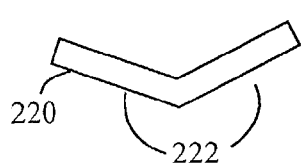
FIG. 50 is a side view of another embodiment of a bent haptic of the present invention.

FIG. 50 is a side view of another embodiment of a bent haptic 220 of the present invention. This haptic 220 comprises two equal segments 222 joined together at an angle.

Figure 51:
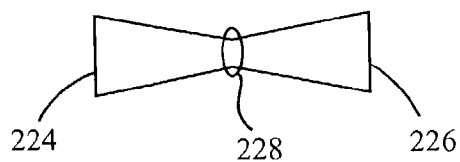
FIG. 51 is a side view of another embodiment of a bent haptic of the present invention.

FIG. 51 is a side view of another embodiment of a bent block haptic 224 of the present invention, which is wider at the ends 226, and narrower in the middle 228. It is noted that this haptic 224 can be hollow, longitudinally.

Figure 52:
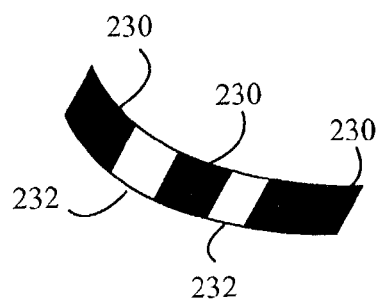
FIG. 52 is a plan view of another embodiment of the present invention wherein the thickness of the haptic is varied longitudinally to form hinge sections.

FIG. 52 is a plan view of another embodiment of the present invention wherein the thickness of the haptic is varied longitudinally to form hinge sections 232, with alternating thick sections 230 and thin sections 232. The thin sections 232 are also hinge sections 232, FIG. 53 is a plan view of another embodiment of the present invention wherein the haptic thickness is varied laterally, but longitudinally constant, with alternating thick sections 234 and thin sections 236.

Figure 53:
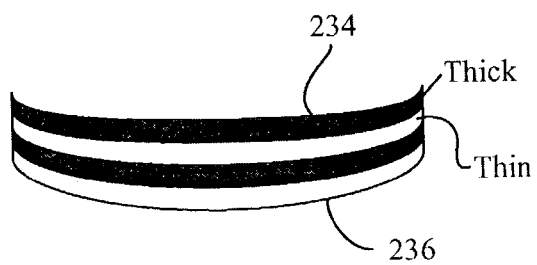
FIG. 53 is a plan view of another embodiment of the present invention wherein the haptic thickness is varied laterally, but longitudinally constant.
Figure 54A:
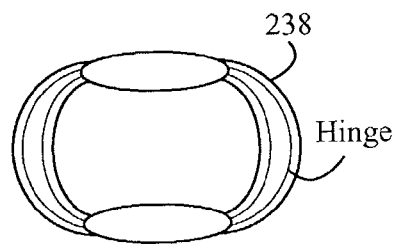
FIG. 54A is a side view of a lens system utilizing the haptic of FIG. 53.

FIG. 54A is a side view of an intraocular lens system utilizing the haptic 238 of FIG. 53.

Figure 54B:
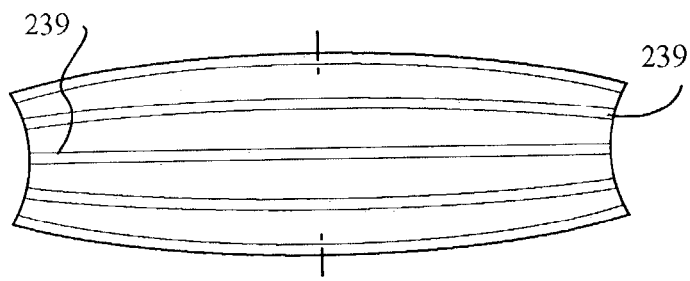
FIG. 54B is a plan view of a haptic that has longitudinally raised pressure ribs.
Figure 54C:
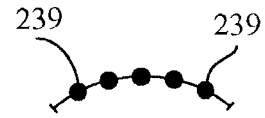
FIG. 54C is a cross-sectional view taken along line 54C of FIG. 54B.

FIGS. 54B and 54C illustrate longitudinally raised projections 239 that provide constant pressure points/lines.

Figure 55:
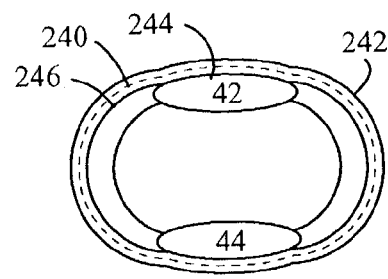
FIG. 55 is a side view of another embodiment of the present invention, the addition of a membrane bag inside the capsular bag.

FIG. 55 is a side view of another embodiment of the present invention, the addition of an artificial membrane bag 240 inside the capsular bag 242 of a person. Specifically, any intraocular lens system having a lens 244 and a haptic 246 is placed inside artificial membrane bag 240. Thus, the artificial membrane bag 240 essentially encapsulates the lens 244 and the haptic 246. This artificial membrane bag 240 is then inserted inside the capsular bag 242 of a patient. The artificial membrane bag 240 can be made from a silicone, hydrogel or other soft, optically transparent material. The artificial membrane bag 240 can further be filled with an optically clear material having a high index of refraction.

The purpose of the artificial membrane bag 240 is to support the capsular bag 242, and to prevent posterior capsular opacification. It is emphasized that a two-lens system is not required for placement in the artificial membrane bag 240.

FIGS. 56-61 illustrate the usage of an annular ledge for a lens. The purpose of the annular ledge is to provide structural support for the lens to make lens distances and configurations possible that were heretofore not possible. The annular ledge is preferably formed from the lens material itself, by taking a larger lens blank and removing material to form a hollow (void) where the hollow separates a lens portion from an annular ledge portion. The lenses may be aspheric, spherical, toric, UV absorb or of Fresnel type, and may further be round, elliptical, or oval.

Figure 56:
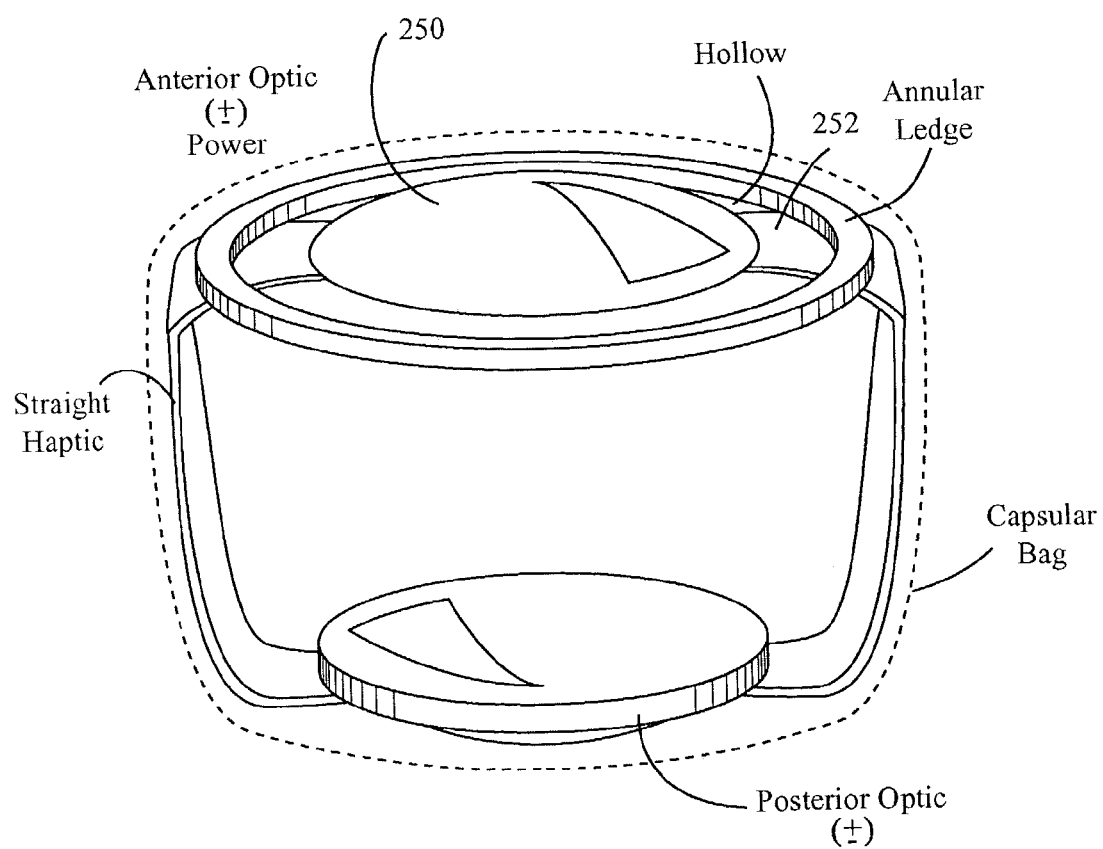
FIG. 56 is a side view of another embodiment of an intraocular lens system of the present invention, wherein an anterior optic lens is provided with an annular ledge.

FIG. 56 is a side view of another embodiment of an intraocular lens system of the present invention, wherein an anterior optic lens 250 is provided with an annular ledge 252, and a hollow portion 254 is formed between annular ledge 252 and lens 250. Lens 250 may be a compressible disk lens.

Figure 57:
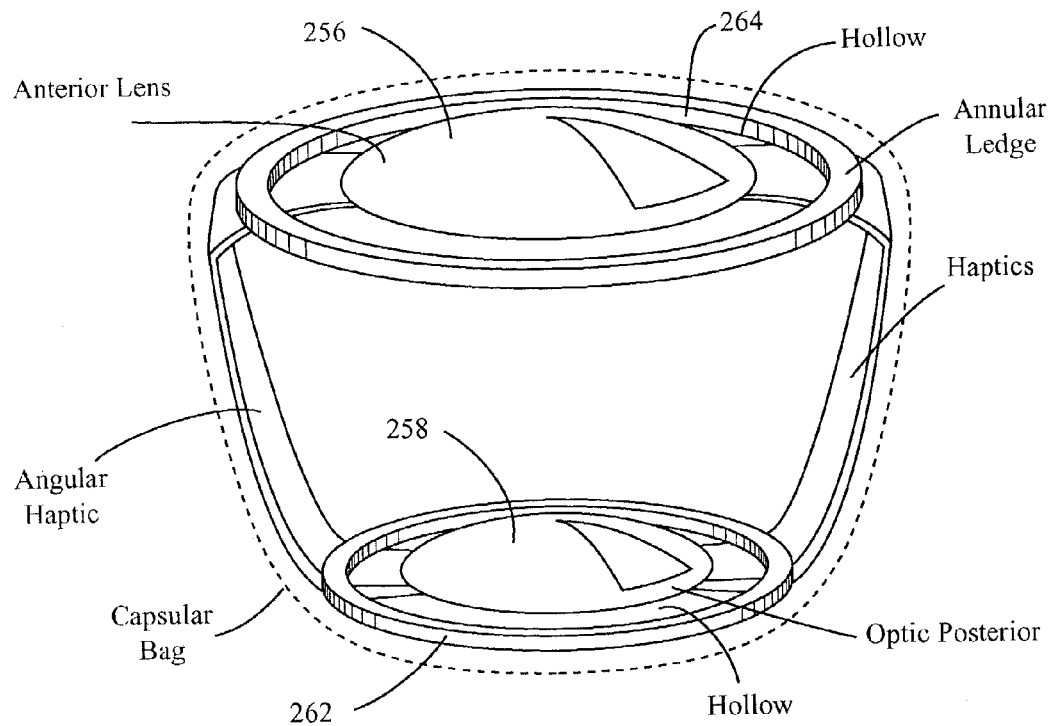
FIG. 57 is a side view of another embodiment of an intraocular lens system of the present invention, wherein lenses of different sizes, each having an annular ledge, is provided.

FIG. 57 is a side view of another embodiment of an intraocular lens system of the present invention, wherein lenses of different sizes 256-258, each having an annular ledge 260 and 262 respectively, is provided, forming a hollow 264 between the lens 256 and annular ledge 260. Lenses 256-258 may be disk lenses.

Figure 58:
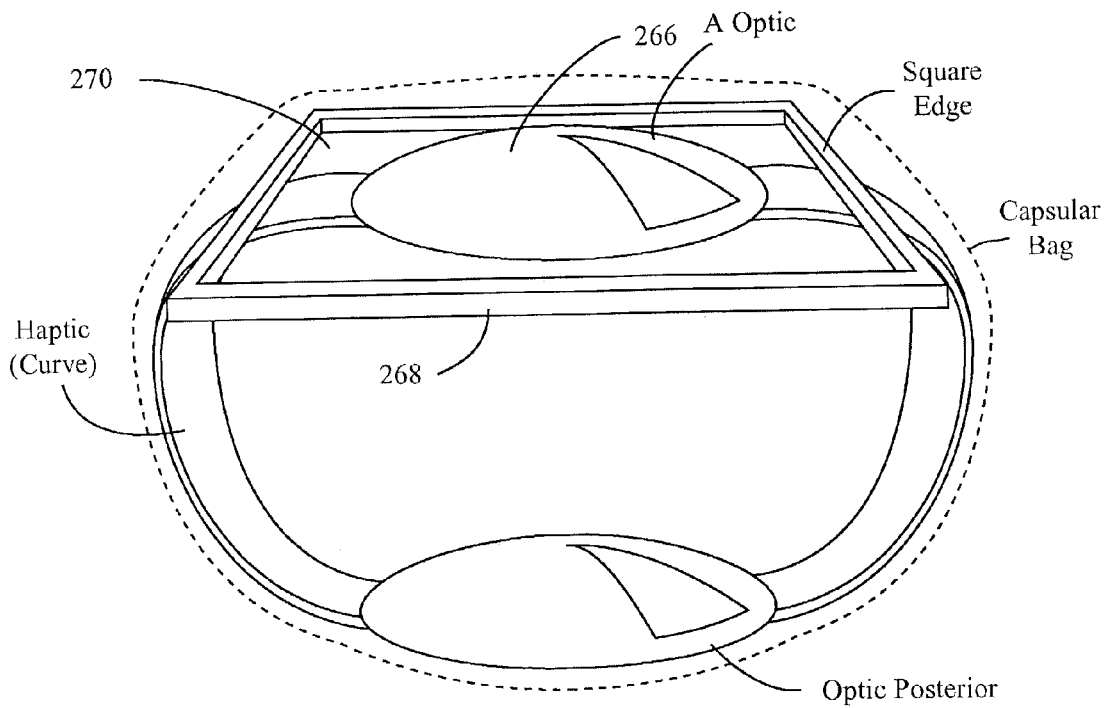
FIG. 58 is a side view of another embodiment of an intraocular lens system of the present invention, wherein the ledge of one lens is provided with a square edge.

FIG. 58 is a side view of another embodiment of an intraocular lens system of the present invention, wherein the ledge 268 of one lens 268 is in the shape of a square, but still with hollow portion 270.

Figure 59:
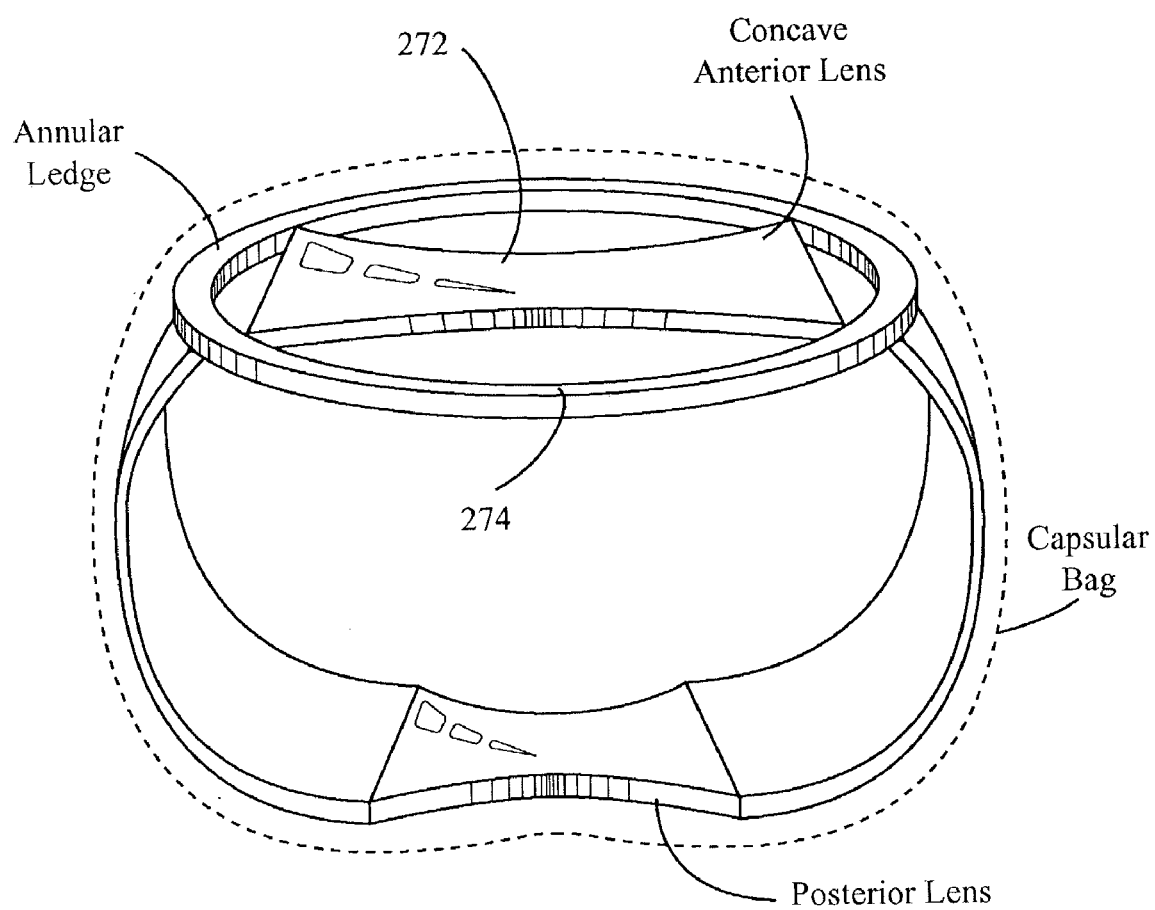
FIG. 59 is a side view of another embodiment of an intraocular lens system of the present invention, wherein one lens is provided with an annular edge ring.

FIG. 59 is a side view of another embodiment of an intraocular lens system of the present invention, wherein one lens 272 is provided with an annular ledge ring 274. As can be seen, the lens 272 may connect to ledge 274 at more than two points, as was the case in prior embodiments. In addition, lens 272 is not required to have an oval, elliptical, round, or generally curved shape, but can assume a variety of various shapes.

Figure 60:
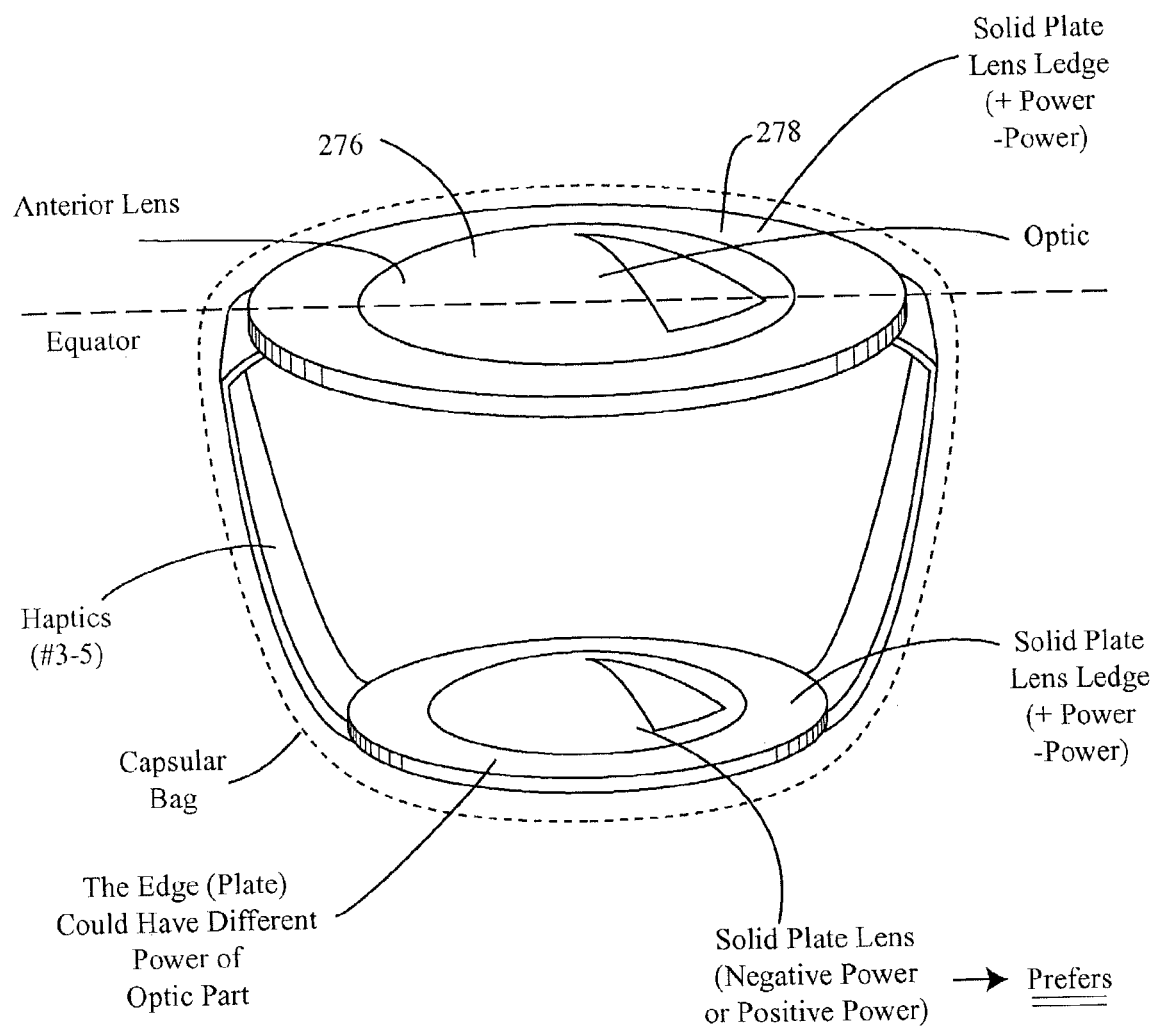
FIG. 60 is a side view of another embodiment of an intraocular lens system of the present invention, wherein one lens is provided with a solid plate ledge having a different optic power than the lens.

FIG. 60 is a side view of another embodiment of an intraocular lens system of the present invention, wherein one lens center 276 is provided with a solid plate ledge 278 having, preferably, a different optic power than the lens (either negative or positive). It is most preferred that the solid plate ledge 278 have a negative optic power relative to lens center 276. It is noted that lens center 276 may be offset in height from solid plate ledge 278 in a manner similar to that of a teacup saucer's center has a different height from the surrounding rim.

Figure 61:
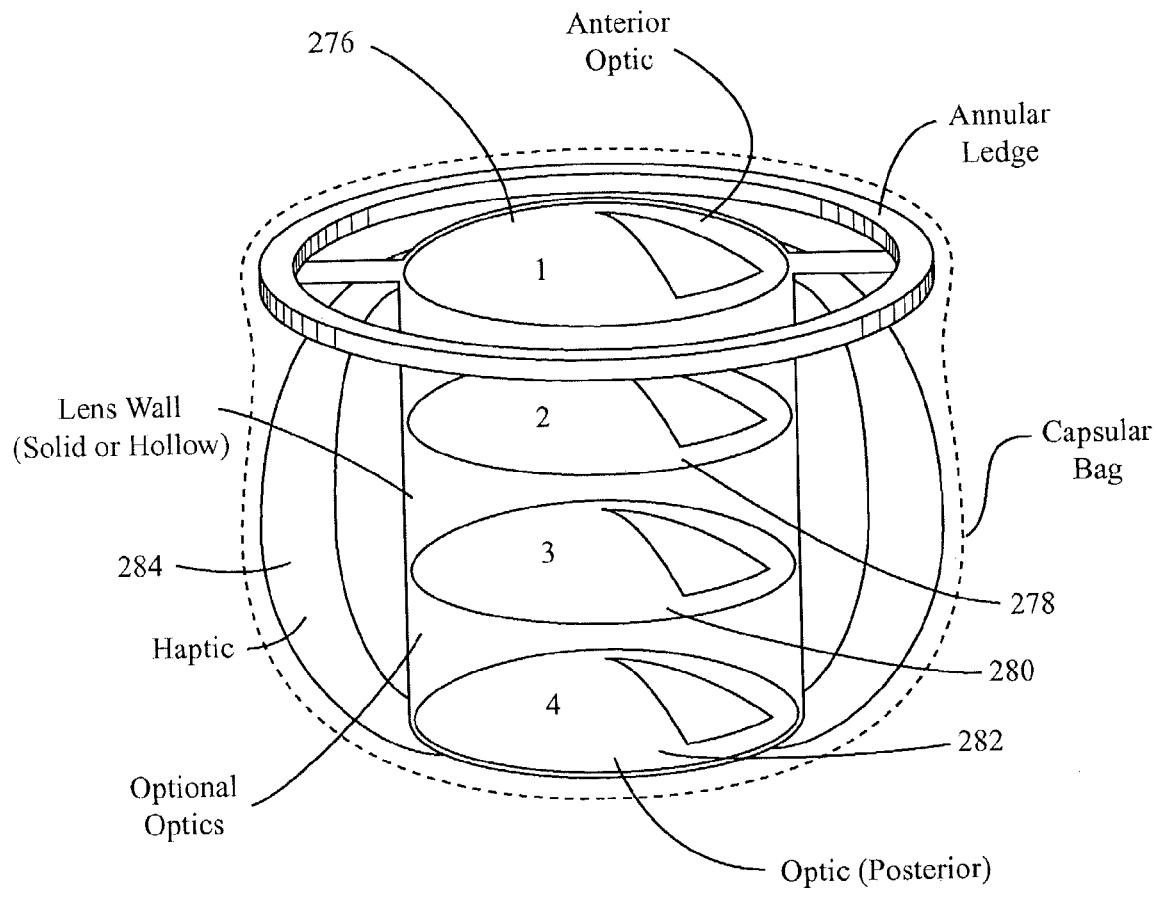
FIG. 61 is a side view of another embodiment of an intraocular lens system of the present invention, utilizing multiple lenses connected by haptics that are compressed in accordion fashion.

FIG. 61 is a side view of another embodiment of an intraocular lens system of the present invention, utilizing multiple lenses 276-282 arranged in cylindrical fashion connected by haptics 284 that may be compressed in accordion fashion. Accordingly, the use of haptic hinged sections discussed above to effect an accordion compression is preferred. Such accordion compression permits a much smaller intraocular lens system package to be inserted into the eye. After insertion into the eye, the package is expanded due to natural haptic mechanical bias. This arrangement would permit correction of greater than 30 diopters.

In any of the embodiments, the attachment of the optic to the haptic may be over, under, tip-to-tip, or slide-in.

In describing the invention, reference has been made to preferred embodiments and illustrative advantages, those skilled in the art, however, and familiar with the instant disclosure of the subject invention, may recognize additions, deletions, modifications, substitutions and/or other changes which will fall within the purview of the subject invention and claims.

After reading and understanding the foregoing description of the invention, in conjunction with the drawings, it will be appreciated that several advantages of the subject improved open chamber, elliptical, accommodative, intraocular lens system are achieved.

In describing the invention, reference has been made to preferred embodiments and illustrative advantages, those skilled in the art, however, and familiar with the instant disclosure of the subject invention, may recognize additions, deletions, modifications, substitutions and/or other changes which will fall within the purview of the subject invention and claims.

What is claimed is:

1. An intraocular lens system, comprising:
   a first positive intraocular lens;
   a second negative intraocular lens;
   a first and a second flexible longitudinally elliptical haptic having ends connected to said first and said second intraocular lenses;
   wherein a visual axis extends through said first and said second intraocular lenses and at said connections with said lenses said first and said second haptics arc outwardly away from said visual axis of said lenses and are disposed longitudinally with said visual axis, which first and second haptics are configured to comprise an inner surface to accommodate an intermediate lens and are disposed to extend in a generally elliptical or circular curve in longitudinal cross-section and operable to follow the contour of the interior surface of an evacuated capsular bag, and wherein the first and second intraocular lenses are configured to be co-axial, whereby motion of said first positive intraocular lens and said second negative intraocular lens with respect to each other along the visual axis changes the overall optical power of said intraocular lens system via ciliary muscles of the eye.

2. A lens system for implantation in an eye, said lens system comprising:
   one positive lens,
   one negative lens, and
   at least three longitudinally elliptical haptics connected to the positive lens and negative lens, wherein the one positive lens and the one negative lens are configured to be co-axial, and wherein a visual axis extends through said positive lens and said negative lens and each haptic arcuately extending from the positive lens and the negative lens and at said connection with said positive lens and said negative lens said haptics arc outwardly away from said visual axis of said lenses and are disposed longitudinally with said visual axis, which the haptics are configured to comprise an inner surface to accommodate an intermediate lens and are disposed to extend in a generally elliptical or circular curve in longitudinal cross-section and operable to follow the contour of the interior surface of an evacuated capsular bag,
   whereby the lens system is adapted such that, when the lens system is positioned in the eye, changes in the ciliary muscle cause motion along the visual axis of the positive lens and the negative lens with respect to each other to reposition said positive lens with respect to said negative lens, whereby the overall optical power of said lens system may be adjusted.

3. An intraocular lens system as described in claim 2 in which said positive lens and said negative lens substantially retain their individual shapes during the repositioning brought about by said motion of said lenses.

4. An intraocular lens system as described in claim 2 in which said positive lens and said negative lens each individually substantially retain their individual optical powers during the repositioning caused by the motion of said lenses.

5. A lens system for implantation in an eye, said lens system comprising:
   one positive lens,
   one negative lens, and
   at least three longitudinally elliptical haptics connected to the positive lens and negative lens, wherein the one positive lens and the one negative lens are configured to be co-axial, and wherein a visual axis extends through said positive lens and said negative lens and each haptic arcuately extending from the positive lens and the negative lens and at said connection with said positive lens and said negative lens said haptics arc outwardly away from said visual axis of said lenses and are disposed longitudinally with said visual axis, which the haptics are configured to comprise an inner surface to accommodate an intermediate lens and are disposed to extend in a generally elliptical or circular curve in longitudinal cross-section and operable to follow the contour of the interior surface of an evacuated capsular bag, whereby motion of the positive lens and the negative lens with respect to each other along the visual axis to reposition said positive lens with respect to said negative lens changes the overall optical power of said lens system via ciliary muscles of the eye.

6. An intraocular lens system as described in claim 5 wherein said positive lens and said negative lens each substantially retains its shape during the repositioning caused by the motion of said lenses.

7. An intraocular lens system as described in claim 5 in which said positive lens and said negative lens each substantially retains its optical power during the repositioning caused by the motion of said lenses.

8. A method for restoring accommodation in an eye, said method comprising:
 providing an intraocular lens system having:
  one positive lens,
  one negative lens, and
  at least three longitudinally elliptical haptics connected to the positive lens and negative lens, wherein the one positive lens and the one negative lens are configured to be co-axial, and wherein a visual axis extends through said positive lens and said negative lens and each haptic arcuately extends from the positive lens and the negative lens and at said connection with said positive lens and said negative lens said haptics arc outwardly away from said visual axis of said lenses and are disposed longitudinally with said visual axis, which the haptics are configured to comprise an inner surface to accommodate an intermediate lens and are disposed to extend in a generally elliptical or circular curve in longitudinal cross-section and operable to follow the contour of the interior surface of an evacuated capsular bag,
  whereby the lens system is adapted such that, when the lens system is positioned in the eye, changes in the ciliary muscle cause motion along the visual axis of the positive lens and the negative lens with respect to each other to cause the repositioning of said positive lens with respect to said negative lens to be altered,
 inserting said lens system in an eye,
 positioning said lens system inside the eye in such a manner that changes in the ciliary muscle will be transmitted to said lens system,
 whereby changes in the tension in the ciliary muscle will effect changes in the overall optical power of said lens system.

9. An accommodative lens system for implantation in an eye, said lens system comprising:
 two lenses;
 at least three longitudinally elliptical haptics connected to said two lenses, wherein the two lenses are configured to be co-axial, and wherein a visual axis extends through said lenses and each haptic arcuately extending from the lenses and at said connection with said two lenses said haptics arc outwardly away from said visual axis of said lenses and are disposed longitudinally with said visual axis, which the haptics are configured to comprise an inner surface to accommodate an intermediate lens and are disposed to extend in a generally elliptical or circular curve in longitudinal cross-section and operable to follow the contour of the interior surface of an evacuated capsular bag, one of said two lenses having positive lens power, the other of said two lenses having negative lens power, wherein the haptics permit axial motion of each lens along the visual axis for repositioning one lens with respect to the other lens, and the overall lens power of said system can be altered by altering the distance between said two lenses.

10. A lens system as described in claim 9, further comprising means whereby the distance between said two lenses can be altered after said lens system has been implanted into an eye.

11. A lens system as described in claim 9, further comprising adjustment means, said adjustment means allowing changes in tension in the ciliary body to be transmitted to said lens system where said changes in tension can be translated into changes of the lens power of said lens system.

12. A lens system as described in claim 9, further comprising adjustment means whereby changes in the tension in the ciliary muscle can reposition said two lenses whereby the lens power of said lens system can be altered.

13. An open, accommodative, intraocular lens system operable to be positioned within the interior of an evacuated capsular bag of a human eye, said intraocular lens system comprising:
 a first, positive lens optic, operable to be positioned within an anterior portion of an evacuated capsular bag of a human eye; and
 a second, negative lens optic, operable to be positioned within a posterior portion of an evacuated capsular bag of a human eye;
 at least three longitudinally elliptical haptics each arcuately connected to the first and second lenses, wherein the first and second lenses are configured to be co-axial, and wherein a visual axis extends through said first and said second lenses and at said connection with said positive lens and said negative lens said haptics arc outwardly away from said visual axis of said lenses and are disposed longitudinally with said visual axis, which the haptics are configured to comprise an inner surface to accommodate an intermediate lens and are disposed to extend in a generally elliptical or circular curve in longitudinal cross-section and operable to follow the contour of the interior surface of an evacuated capsular bag; and
 wherein said first, positive lens optic and said second, negative lens optic are coupled to move responsively to ciliary muscles in the eye in a direction toward and away from each other along the visual axis when the lens optics are in the capsular bag.

14. The intraocular lens system of claim 13, comprising at least four haptics.

15. The intraocular lens system of claim 13, comprising at least five haptics.

16. The intraocular lens system of claim 13, wherein said haptics are longitudinally arcuate when viewed in a direction normal to an anterior face of said first, positive lens optic, said haptics extending outwardly from a periphery of the first, positive lens optic at an angle of approximately 30-40 degrees, and said haptics are equally spaced about the periphery of said first, positive lens optic.

17. The intraocular lens system of claim 13 wherein said haptics when viewed in longitudinal cross-section are elliptical with a ratio of ellipse of approximately 0.96.

18. The intraocular lens system of claim 13 wherein the cross section configuration of each haptic transverse to the direction of the optic axis is substantially a circular arc having a radius of curvature of approximately 4.5 mm.

* * * * *